(12) United States Patent
Natarajan et al.

(10) Patent No.: US 9,211,176 B2
(45) Date of Patent: Dec. 15, 2015

(54) ADHESIVE STRUCTURE WITH STIFF PROTRUSIONS ON ADHESIVE SURFACE

(71) Applicants: ETHICON ENDO-SURGERY, INC., Cincinnati, OH (US); Agency for Science Technology and Research, Connexis (SG)

(72) Inventors: Sriram Natarajan, Hillsborough, NJ (US); Joseph Hammer, Hillsborough, NJ (US); Kevin Cooper, Flemington, NJ (US); Murty Vyakarnam, Bridgewater, NJ (US); Hong Yee Low, Botannia (SG); Isabel Rodriguez, Singapore (SG); Chee Tiong Lim, Singapore (SG); Audrey Yoke Yee Ho, Crescent (SG)

(73) Assignees: ETHICON ENDO-SURGERY, INC., Cincinnati, OH (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 326 days.

(21) Appl. No.: 13/841,561

(22) Filed: Mar. 15, 2013

(65) Prior Publication Data
US 2013/0206330 A1     Aug. 15, 2013

Related U.S. Application Data

(60) Division of application No. 13/340,331, filed on Dec. 29, 2011, now abandoned, which is a continuation-in-part of application No. 12/871,745, filed on Aug. 30, 2010, now abandoned.

(51) Int. Cl.
*A61F 2/00* (2006.01)
*A61L 31/04* (2006.01)
(Continued)

(52) U.S. Cl.
CPC ............. *A61F 2/0063* (2013.01); *A61L 31/048* (2013.01); *A61L 31/06* (2013.01); *A61L 31/10* (2013.01);
(Continued)

(58) Field of Classification Search
USPC .................................................. 264/317, 41
See application file for complete search history.

(56) References Cited

U.S. PATENT DOCUMENTS

| 4,256,693 A | 3/1981 | Kondo et al. |
| 4,464,254 A | 8/1984 | Dojki et al. |

(Continued)

FOREIGN PATENT DOCUMENTS

| DE | 4126877 C1 | 11/1992 |
| DE | 19832634 A1 | 1/2000 |

(Continued)

OTHER PUBLICATIONS

S.D. Lee, "Surface Modification of Polypropylene Under Argon and Oxygen-RF-Plasma Conditions", Plasmas and Polymers, vol. 2, No. 3, Sep. 1, 1997, pp. 177-198.
(Continued)

*Primary Examiner* — Yogendra Gupta
*Assistant Examiner* — Kimberly A Stewart
(74) *Attorney, Agent, or Firm* — Roberts Mlotkowski Safran & Cole, P.C.

(57) ABSTRACT

A laminate and process of making the laminate is disclosed comprising: a surgical mesh having first and second surfaces; and an adhesive structure having adhesive and non-adhesive surfaces, wherein the non-adhesive surface of the adhesive structure is laminated to at least one of said first and second surfaces of said surgical mesh, and the adhesive surface of said adhesive structure has protrusions extending therefrom comprising a resin having a Young's modulus of greater than 17 MPa, which protrusions are of sufficiently low diameter to promote adhesion by increasing physical attractive forces between the adhesive structure and a target surface, as measured by shear adhesion.

2 Claims, 15 Drawing Sheets

(51) Int. Cl.
*A61L 31/06* (2006.01)
*B29C 33/52* (2006.01)
*C09J 7/04* (2006.01)
*A61L 31/10* (2006.01)
*A61B 17/00* (2006.01)

(52) U.S. Cl.
CPC ............... *B29C 33/52* (2013.01); *C09J 7/041* (2013.01); *A61B 2017/00871* (2013.01); *A61B 2017/00938* (2013.01); *A61B 2017/00942* (2013.01); *A61B 2017/00951* (2013.01); *C09J 2201/32* (2013.01); *C09J 2400/263* (2013.01)

(56) References Cited

U.S. PATENT DOCUMENTS

| | | | |
|---|---|---|---|
| 4,557,264 A | 12/1985 | Hinsch | |
| 4,753,776 A | 6/1988 | Hillman et al. | |
| 4,911,165 A | 3/1990 | Lennard et al. | |
| 5,011,494 A | 4/1991 | von Recum et al. | |
| 5,176,692 A | 1/1993 | Wilk et al. | |
| 5,246,451 A | 9/1993 | Trescony et al. | |
| 5,246,666 A | 9/1993 | Vogler et al. | |
| 5,324,519 A | 6/1994 | Dunn et al. | |
| 5,344,611 A | 9/1994 | Volger et al. | |
| 5,455,009 A | 10/1995 | Volger et al. | |
| 5,569,272 A | 10/1996 | Reed et al. | |
| 5,723,219 A | 3/1998 | Kolluri et al. | |
| 6,217,540 B1 | 4/2001 | Yazawa et al. | |
| 6,220,453 B1 | 4/2001 | Kitajima et al. | |
| 6,267,772 B1 | 7/2001 | Mulhauser et al. | |
| 6,368,871 B1 | 4/2002 | Christel et al. | |
| 6,403,655 B1 | 6/2002 | Bezwada et al. | |
| 6,485,503 B2 | 11/2002 | Jacobs et al. | |
| 6,638,284 B1 | 10/2003 | Rousseau et al. | |
| 6,703,041 B2 * | 3/2004 | Burns et al. | 424/444 |
| 6,720,469 B1 | 4/2004 | Curtis et al. | |
| 6,872,439 B2 | 3/2005 | Fearing et al. | |
| 6,913,697 B2 | 7/2005 | Lopez et al. | |
| 7,074,294 B2 | 7/2006 | Dubrow | |
| 7,195,872 B2 | 3/2007 | Agrawal et al. | |
| 7,331,199 B2 | 2/2008 | Ory et al. | |
| 7,479,318 B2 | 1/2009 | Jagota et al. | |
| 7,745,223 B2 | 6/2010 | Schubert et al. | |
| 7,754,233 B2 | 7/2010 | Andjelic et al. | |
| 7,988,733 B2 | 8/2011 | Shimp et al. | |
| 8,133,484 B2 | 3/2012 | Preiss-Bloom et al. | |
| 8,307,831 B2 | 11/2012 | Rousseau | |
| 2003/0208888 A1 | 11/2003 | Fearing et al. | |
| 2004/0076822 A1 | 4/2004 | Jagota et al. | |
| 2004/0125266 A1 | 7/2004 | Miyauchi et al. | |
| 2005/0095699 A1 | 5/2005 | Miyauchi et al. | |
| 2005/0106552 A1 | 5/2005 | Ikeda | |
| 2005/0181629 A1 | 8/2005 | Jagota et al. | |
| 2006/0005362 A1 | 1/2006 | Arzt et al. | |
| 2006/0034734 A1 | 2/2006 | Schubert et al. | |
| 2006/0078724 A1 | 4/2006 | Bhushan et al. | |
| 2006/0087053 A1 | 4/2006 | O'Donnell et al. | |
| 2006/0154063 A1 | 7/2006 | Fujihara et al. | |
| 2006/0204738 A1 | 9/2006 | Dubrow et al. | |
| 2007/0227967 A1 | 10/2007 | Sakaino et al. | |
| 2007/0299542 A1 | 12/2007 | Mathisen et al. | |
| 2008/0124246 A1 | 5/2008 | Diaz-Quijada et al. | |
| 2008/0217180 A1 | 9/2008 | Doye et al. | |
| 2008/0241512 A1 | 10/2008 | Boris et al. | |
| 2008/0241926 A1 | 10/2008 | Lee et al. | |
| 2008/0280085 A1 | 11/2008 | Livne | |
| 2009/0130372 A1 | 5/2009 | Fukui et al. | |
| 2009/0318843 A1 | 12/2009 | Van Holten et al. | |
| 2010/0098909 A1 | 4/2010 | Reyssat et al. | |
| 2010/0137903 A1 | 6/2010 | Lee et al. | |
| 2010/0249913 A1 * | 9/2010 | Datta et al. | 623/1.39 |
| 2011/0021965 A1 | 1/2011 | Karp et al. | |
| 2011/0063610 A1 | 3/2011 | Ivanov et al. | |
| 2011/0160869 A1 | 6/2011 | Duch et al. | |
| 2011/0172760 A1 | 7/2011 | Anderson | |
| 2011/0177288 A1 | 7/2011 | Bhushan et al. | |
| 2011/0282444 A1 | 11/2011 | Liu et al. | |
| 2011/0293667 A1 | 12/2011 | Baksh et al. | |
| 2012/0052234 A1 | 3/2012 | Natarajan et al. | |
| 2012/0143228 A1 | 6/2012 | Natarajan et al. | |
| 2012/0251611 A1 | 10/2012 | Luong-Van et al. | |
| 2012/0302427 A1 | 11/2012 | Elmouelhi et al. | |
| 2012/0302465 A1 | 11/2012 | Elmouelhi et al. | |
| 2013/0172927 A1 | 7/2013 | Natarajan et al. | |
| 2013/0266761 A1 | 10/2013 | Ho et al. | |
| 2013/0267880 A1 | 10/2013 | Luong-Van et al. | |
| 2013/0288225 A1 | 10/2013 | Elmouelhi et al. | |
| 2014/0120314 A1 | 5/2014 | Ho et al. | |

FOREIGN PATENT DOCUMENTS

| | | |
|---|---|---|
| EP | 1416303 | 5/2004 |
| JP | 2004170935 A | 6/2004 |
| JP | 2013-226413 A | 11/2013 |
| SG | 193370 A | 10/2013 |
| WO | 0056808 | 9/2000 |
| WO | 03/099160 A1 | 12/2003 |
| WO | 2004/094303 A2 | 11/2004 |
| WO | 2006031197 | 3/2006 |
| WO | 2008/076390 A3 | 6/2008 |
| WO | 2008/102620 A1 | 8/2008 |
| WO | 2009022911 A2 | 2/2009 |
| WO | 2009029045 | 3/2009 |
| WO | 2009/067482 A1 | 5/2009 |
| WO | 2009/123739 A1 | 10/2009 |
| WO | 2010/129641 A1 | 11/2010 |
| WO | 2011/026987 A1 | 3/2011 |
| WO | WO 2012/030570 A1 | 3/2012 |
| WO | WO 2012/162452 A2 | 11/2012 |
| WO | WO 2013/102085 A1 | 7/2013 |
| WO | WO 2013/163304 A1 | 10/2013 |

OTHER PUBLICATIONS

International Search Report for PCT/US2013/038007 dated Jun. 18, 2013.
Sriram Natarajan, U.S. Appl. No. 12/871,745, filed Aug. 30, 2010.
Noha Elmouelhi, U.S. Appl. No. 13/116,721, filed May 26, 2011.
Sriram Natarajan, PCT No. PCT/US2011/048584 Filed Aug. 22, 2011.
Sriram Natarajan, U.S. Appl. No. 13/340,331, filed Dec. 29, 2011.
Noha Elmouelhi, U.S. Appl. No. 13/340,405, filed Dec. 29, 2011.
Emma Kim Luong-Van, U.S. Appl. No. 13/435,544, filed Mar. 30, 2012.
Audrey Yoke Yee Ho, U.S. Appl. No. 13/441,496, filed Apr. 6, 2012.
Emma Kim Luong-Van, U.S. Appl. No. 13/441,539, filed Apr. 6, 2012.
Noha Elmouelhi, U.S. Appl. No. 13/458,825, filed Apr. 27, 2012.
Noha Elmouelhi, PCT No. PCT/US2012/039256 filed May 12, 2012.
Sriram Natarajan, U.S. Appl. No. 13/730,259, filed Dec. 28, 2012.
Sriram Natarajan, PCT No. PCT/US2012/072081 filed Dec. 28, 2012.
Noha Elmouelhi, PCT No. PCT/US2013/038007 filed Apr. 24, 2013.
Audrey Yoke Yee Ho, U.S. Appl. No. 14/139,673, filed Dec. 23, 2013.
Search Report of Singapore Patent Application No. 2013086434 dated Dec. 4, 2014.
Written Opinion of Singapore Patent Application No. 2013086434 dated Jan. 16, 2015.
Chang, T.C., Plasma Surface Treatment in Composites Manufacturing, Journal of Industrial Technology, Nov. 1, 1998-Jan. 1999, vol. 15, No. 1, pp. 1-7, Table 1.
U.S. Appl. No. 12/871,745, filed Aug. 30, 2010.
U.S. Appl. No. 13/116,721, filed May 26, 2011.
U.S. Appl. No. 13/340,331, filed Dec. 29, 2011.
U.S. Appl. No. 13/340,405, filed Dec. 29, 2011.
U.S. Appl. No. 13/435,544, filed Mar. 30, 2012.
U.S. Appl. No. 13/441,496, filed Apr. 6, 2012.
U.S. Appl. No. 13/441,539, filed Apr. 6, 2012.
U.S. Appl. No. 13/458,825, filed Apr. 27, 2012.

(56) References Cited

OTHER PUBLICATIONS

International Search report for International Application No. PCT/US2011/048584 dated Feb. 20, 2012.
International Search report for International Application No. PCT/US2012/072081 dated Mar. 12, 2013.
Messina G.M.L., et al., "A multitechnique study of preferential protein adsorption on hydrophobic and hydrophilic plasma-modified polymer surfaces", Colloids and Surfaces. B., Biointerfaces, vol. 70, No. 1, Apr. 1, 2009, pp. 76-83.
Chen H. et al., "The effect of surface microtopography of poly (dimethylsiloxane) on protein adsorption, platelet and cell adhesion", Colloids and Surfaces. B., Biointerfaces, vol. 71, No. 2, Jul. 1, 2009, pp. 275-281.
Saez et al., "Rigidity-driven growth and migration of epithelial cells on microstructured anisotropic substrates", PNAS, vol. 104, No. 20, pp. 8281-8286, May 15, 2007.
Oxford Dictionary Online Definition of "Cylinder", dated Jun. 11, 2013.
Definition of "Integral", Merriam-Webster Dictionary online, pp. 1-3, Accessed Oct. 15, 2013.
Anthony G. Gristina, "Biomaterial-Centered Infection: Microbial Adhesion Versus Tissue Integration", Science, vol. 237, pp. 1588-1595 (1987).
Ji Yeong Won et al., "The Fabrication of Protein Nano Arrays Using 3-Dimensional Plastic Nanopillar Patterns", Nanoscience and Nanotechnology, vol. 11, pp. 4231-4235 (2011).
Ning Zhao et al., "Self-organized Polymer Aggregates with a Biomimetic Hierarchical Structure and its Superhydrophobic Effect", Cell Biochem Biophys, vol. 49, pp. 91-97 (2007).
Bharat Bhushan et al., "Self-Cleaning Efficiency of Artificial Superhydrophobic Surfaces" Langmuir, vol. 25, No. 5, pp. 3240-3248 (2009).
Jun Shi et al., "Towards Bioinspired Superhydrophobic Ply(L-lactiv acid) Surfaces Using Phase Inversion-Based Methods", Bioinspiration & Biomimetics, vol. 3, pp. 1-6 (2008).
Yong Chae Jung et al., "Wetting Behavior of Water and Oil Droplets in Three-Phase Interfaces for Hydrophobicity/philicity and Oleophobicity/philicity", Langmuir, vol. 25 (24), pp. 14165-14173 (2009).
Yuwon Lee et al., "Fabrication of Hierarchical Structures on a Polymer Surface to Mimic Natural Superhydrophobic Surfaces", Advanced Materials, vol. 19, pp. 2330-2335 (2007).
Kyoung Je Cha et al., "Effect of Replicated Polymeric Substrate with Lotus Surface Structure on Adipose-Derived Stem Cell Behaviors", Macromoleculare Bioscience, vol. 11, pp. 1357-1363 (2011).
Takashi Yanagishita et al., "Anti-Reflection Structures on Lenses by Nanoimprinting Using Ordered Anodic Porous Alumina", Applied Physics Express 2, pp. 022001-1-022001-3 (2009).
Anna J. Schulte et al., "Hierarchically Structured Superhydrophobic Flowers with Low Hysteresis of the Wild Pansy (Viola Tricolor)—New Design Principles for Biomimetic Materials", Beilstein J. Nanotechnol, vol. 2, pp. 228-236 (2011).
Bharat Bhushan et al., "Micro-, Nano- and Hierarchical Structures for Superhydrophobicity, Self-Cleaning and Low Adhesion", Philosophical Transaction of the Royal Society, A (2009) 367, pp. 1631-1672. Downloaded from rsta.royalsocietypublishing.org on Mar. 2, 2012.
Sitti M. et al., High aspect ratio polymer micro/nano-structure manufacturing using nanoembossing, nanomolding and directed self-assembly; IEEE/ASME Advanced Mechatronics Conference, Kobe, Japan, Jul. 2003.
Tsougeni K. et al., Nano-texturing of poly(methyl methacrylate) polymer using plasma processes and applications in wetting control and protein adsorption; Journal Microelectronic Engineering, vol. 86 (2009) 1424-1427.
Vlachopoulou M.-E. et al., Effect of surface nanostructuring of PDMS on wetting properties, hydrophobic recovery and protein adsorption, Microelectronic Engineering,vol. 86, (2009) 1321-1324.
Occhiello, et al., "Oxygen-Plasma-Treated Polypropylene Interfaces with Air, Water, and Epoxy Resins: Part 1. Air and Water.", 1991, Journal of Applied Polymer Science, 42, pp. 551-559.
Gerard, et al., "Surface modification of polypropylene membranes used for blood filtration", 2011, Polymer, 52, pp. 1223-1233.
Roure, et al., "Force Mapping in Epithelial Cell Migration", pp. 2390-2395, PNAS, Feb. 15, 2005, vol. 102, No. 7.
Oxford Dictionary Online Definition of "Cylinder".
International Search Report for PCT/US2012/039256 dated Mar. 5, 2013.
Wan Y., et al., "Characterization of surface property of poly (lactide-co-glycolide) after oxygen plasma treatment", Biomaterials, Elsevier Science Publishers, vol. 25, No. 19, Aug. 1, 2004, pp. 4777-4783.
Jianhua Wei, et al., "Influence of surface wettability on competitive protein adsorption and initial attachment of osteoblasts; Competitive protein adsorption and initial cell attachment", Biomedical Materials, Institute of Physics Publishing, vol. 4, No. 4, Aug. 1, 2009, p. 45002.
Tsougeni K., et al., "Mechanisms of oxygen plasma nanotexturing of organic polymer surfaces: From stable super hydrophilic to super hydrophobic surfaces", Langmuir, American Chemical Society, vol. 25, No. 19, Oct. 6, 2009, pp. 11748-11759.
Office Action dated May 22, 2015 in U.S. Appl. No. 13/116,721; 27 pages.
Office Action dated May 22, 2015 in U.S. Appl. No. 13/340,405; 30 pages.
Office Action dated Jun. 4, 2015 in U.S. Appl. No. 13/730,259; 11 pages.

\* cited by examiner

ADHESIVE STRUCTURE WITH STIFF PROTRUSIONS ON ADHESIVE SURFACE

This application is a divisional of U.S. application Ser. No. 13/340,331, filed Dec. 29, 2011, which is a continuation-in-part of, and claims the benefit of priority under 35 U.S.C. §120 to U.S. application Ser. No. 12/871,745, filed Aug. 30, 2010, the disclosures of each are hereby incorporated by reference herein in their entirety.

FIELD OF THE INVENTION

The present invention relates to polymer-based structures having shapes and mechanical properties that optimize adhesion to a specific target, e.g., a tissue or organ target.

BACKGROUND OF THE INVENTION

There is an ongoing need for adhesive structures having improved adhesion obtained through physical attractive forces. Such structures can be suited to use in various applications, such as medical applications, e.g., as an adjunct or replacement to sutures and staples used to close surgical incisions. For the adhered to substrate, e.g., living tissue, providing an adhesive structure that provides adhesive forces by non-chemical interactions between adhesive structure and substrate would be highly desirable.

Intermolecular forces are exerted by molecules on each other and affect the macroscopic properties of the material of which the molecules are a part. Such forces may be either attractive or repulsive in nature. They are conveniently divided into two classes: short-range forces, which operate when the centers of the molecules are separated by 3 angstroms or less, and long-range forces, which operate over greater distances.

Generally, if molecules do not interact chemically, the short-range forces between them are repulsive. These forces arise from interactions of the electrons associated with the molecules and are also known as exchange forces. Molecules that interact chemically have attractive exchange forces, also known as valence forces. Mechanical rigidity of molecules and effects such as limited compressibility of matter arise from repulsive exchange forces.

For present purposes, physical attractive forces are considered to be attractive forces that are not chemical in nature, e.g., not dependent on or associated with ionic bonding, covalent bonding, or hydrogen bonding. Physical attractive forces can include long-range forces or van der Waals forces as they are also called. These forces account for a wide range of physical phenomena, such as friction, surface tension (capillary actions), adhesion and cohesion of liquids and solids, viscosity and the discrepancies between the actual behavior of gases and that predicted by the ideal gas law. Typical bond energies from van der Waals forces are about 1 kcal/mol compared to about 6 kcal/mol for hydrogen bonds and about 80 kcal/mol for carbon-to-carbon bonds. Van der Waals forces arise in a number of ways, one being the tendency of electrically polarized molecules to become aligned. Quantum theory indicates also that in some cases the electrostatic fields associated with electrons in neighboring molecules constrain the electrons to move more or less in phase.

The London dispersion force otherwise known as quantum induced instantaneous polarization (one of the three types of van der Waals forces) is caused by instantaneous changes in the dipole of atoms, resulting from the location of the electrons in the atoms' orbitals. When an electron is on one side of the nucleus, this side becomes slightly negative (indicated by $\delta-$); this in turn repels electrons in neighboring atoms, making these regions slightly positive ($\delta+$). This induced dipole causes a brief electrostatic attraction between the two molecules. The electron immediately moves to another point and the electrostatic attraction is broken. London dispersion forces are typically very weak because the attractions are so quickly broken, and the charges involved are so small.

Despite the weakness of van der Waals forces, it has been recognized that such forces can contribute to adhesion by a structure formed in nature. For example, it has been observed that the adhesive force of a gecko's foot is attributable to the van der Waals forces generated by hundreds of thousands of fibrillar, hair-like microstructures known as setae, which terminate in even smaller structures (200 to 400 nanometers in diameter) known as spatulae. Such structure permits a gecko to climb even smooth surfaces such as vertical planes of glass, achieving adhesion without any requirement that the target substrate itself provide adhesive characteristics. Structures mimicking a gecko's foot have been attempted by various methods including nano-molding using a template, polymer self-assembly, lithography, and etching. However, such structures are inherently delicate and can suffer from durability problems in practical applications. Accordingly, structures offering adhesion attributable to van der Waals forces but with simpler shapes and construction are desirable.

U.S. Pat. No. 6,872,439 proposes a fabricated microstructure comprising at least one protrusion capable of providing an adhesive force at a surface of between about 60 and 2,000 nano-Newtons. A stalk supports the protrusion at an oblique angle relative to a supporting surface, and the microstructure can adhere to different surfaces.

U.S. Pat. No. 7,479,318 relates to a fibrillar microstructure and processes for its manufacture. These processes involve micromachining and molding, and can be used to prepare sub-micron dimensioned fibrillar microstructures of any shape from polymeric as well as other materials.

WO 2008/076390 teaches dry adhesives and a method for forming a dry adhesive structure on a substrate by forming a template backing layer of energy sensitive material on the substrate, forming a template layer of energy sensitive material on the template backing layer, exposing the template layer to a predetermined pattern of energy, removing a portion of the template layer exposed to the predetermined pattern of energy, and leaving a template structure formed from energy sensitive material and connected to the substrate through the template backing layer.

WO 2009/067482 proposes an adhesive article that includes a biocompatible and at least partially biodegradable substrate having a surface; and a plurality of protrusions extending from the surface. The protrusions include a biocompatible and at least partially biodegradable material, and have an average height of less than approximately 1,000 micrometers.

A review of the prior art shows use of micro-nano structures on polymer substrates for adhesion to tissue (WO 2009/067482), but the materials used to fabricate these structures comprise "softer" polymers, i.e., polymers or polymer mixtures having a Young's modulus ≤17 MPa. Moreover, they do not provide a solution for adhesion to specific types of tissue.

It would be desirable to provide an adhesive structure without relying solely on surface chemical groups to provide acceptable conformal contact and adhesion with its intended target surface.

It would also be desirable to provide an adhesive structure that has a stiffness (Young's modulus) greater than 17 MPa that provides a means by which a fluid such as the tissue's own fluid or a chemical group such as a fibrin sealant can wick into the structure to enhance adhesion with its intended target surface.

SUMMARY OF THE INVENTION

The present invention relates to a laminate comprising: a (polymeric) surgical mesh having first and second surfaces; and an adhesive structure having adhesive and non-adhesive surfaces, wherein the non-adhesive surface of the adhesive structure is laminated to at least one of said first and second surfaces of said surgical mesh, and the adhesive surface of said adhesive structure has protrusions extending therefrom comprising a resin having a Young's modulus of greater than 17 MPa, which protrusions are of sufficiently low diameter to promote adhesion by increasing physical attractive forces between the adhesive structure and a target surface, as measured by shear adhesion.

In another embodiment, the present invention is directed to a method of forming a laminate of a surgical mesh having first and second surfaces, and an adhesive structure having adhesive and non-adhesive surfaces, comprising: a) providing a first specific solvent-dissolvable mold including indentations; b) providing a first meltable polymer having a Young's modulus of greater than 17 MPa to the first mold under conditions sufficient to permit filling the indentations of the first mold by the first polymer, said first polymer being substantially non-dissolvable by the specific solvent; c) treating the first mold and first polymer of step b) to an extent sufficient to substantially solidify the first polymer; d) laminating a surgical mesh, also non-dissolvable by said specific solvent, to an exposed surface of said first meltable polymer at the top of said first mold; and e) exposing the first mold, first polymer and surgical mesh to the specific solvent under mold-dissolving conditions to dissolve said first mold.

DETAILED DESCRIPTION

Figure 1:
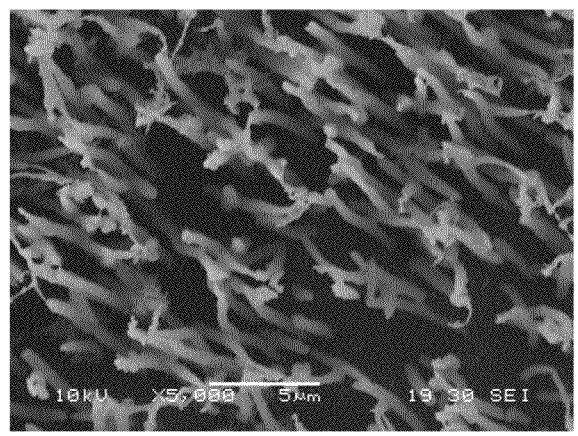
FIG. 1 is a scanning electron microscope image of a polypropylene substrate with micropillars of 1 micron diameter×20 microns length.

Young's modulus (E) is a measure of the stiffness of an isotropic elastic material. It is also known as the Young modulus, modulus of elasticity, elastic modulus (though Young's modulus is actually one of several elastic moduli such as the bulk modulus and the shear modulus) or tensile modulus. It is defined as the ratio of the uniaxial stress over the uniaxial strain in the range of stress in which Hooke's Law holds. This can be experimentally determined from the slope of a stress-strain curve created during tensile tests conducted on a sample of the material. Young's modulus quantifies the elasticity of the polymer. It is defined, for small strains, as the ratio of rate of change of stress to strain. Like tensile strength, this is highly relevant in polymer applications involving the physical properties of polymers, such as rubber bands. The modulus is strongly dependent on temperature.

Young's modulus, E, can be calculated by dividing the tensile stress by the tensile strain:

$$E \equiv \frac{\text{tensile stress}}{\text{tensile strain}} = \frac{\sigma}{\varepsilon} = \frac{F/A_0}{\Delta L/L_0} = \frac{FL_0}{A_0 \Delta L}$$

where
E is the Young's modulus (modulus of elasticity)
F is the force applied to the object;
$A_0$ is the original cross-sectional area through which the force is applied;
$\Delta L$ is the amount by which the length of the object changes;
$L_0$ is the original length of the object.

For present purposes, Young's modulus can be measured in accordance with ASTM standard D412-98a.

For present purposes, target surface roughness can be defined as the average longest dimension of the particles or microstructures that provide roughness to a surface of the target. For a spherical or roughly spherical shape, the diameter can be considered the longest dimension. Standard surface roughness analysis can be carried out by microscopy techniques such as scanning electron microscopy (SEM), atomic force microscopy (AFM) and optical interferometric profiling. Another method of determining roughness is by comparison of a surface with silicon carbide grinding papers of different FEPA (Federation of European Producers Association) surface roughnesses—P#4000 (3 microns size grains), P#2400 (8 microns size grains) and P#500 (30 microns size grains). These grains are roughly spherical and their size determined by their largest dimension.

For purposes of the present invention, a target surface can include biological tissue, or non-tissue, e.g., a surface associated with a medical device or prosthetic. In certain embodiments, the target surface can be associated with the adhesive structure itself, e.g., in the case of a substrate or film comprising protrusions on either side, which can be utilized as a double-sided adhesive tape. Such a double-sided embodiment can even be wrapped around itself or a similar adhesive structure, to provide adhesion at least partially promoted by physical attractive forces.

The polymer substrates of which the structures are made are typically stiff, with a Young's modulus greater than 17 MPa, and can be hydrophilic or hydrophobic. The dimensions of the nanostructures are engineered for adhesion to specific targets with a diameter from 0.1-5 microns and height greater than 1 micron. The dimensions are tailored to match the dimensions of the substrate so that maximum adhesion can be had. Polymers used may be biodurable such as polypropylene (PP) or bioabsorbable such as poly(lactic-co-glycolic acid) (PLGA) and polydioxanone (PDO).

As earlier noted, in one aspect the present invention relates to an adhesive structure which is a laminate comprising a surgical mesh having first and second surfaces, and an adhesive structure having an adhesive surface from which extend protrusions comprising a resin having a Young's modulus of greater than 17 MPa, which protrusions are of sufficiently low diameter to promote adhesion by increasing physical attractive forces, e.g., Van der Waals attractive forces between the adhesive structure and a target surface, as measured by shear adhesion, and a non-adhesive surface.

In one embodiment, the protrusions have an average diameter ranging from 0.2 to 5 microns, an average length greater than 1 micron and an aspect ratio (length/diameter) of 1 to 33

In another embodiment, the protrusions have an average diameter ranging from 0.2 to 2 microns, an average length greater than 3 microns and an aspect ratio (length/diameter) of 2 to 30.

In still another embodiment, the adhesive structure is integrally molded from a resin selected from at least one of thermoplastic resin, thermosetting resin, and curable resin. By integrally molded is meant that the structure is formed in one piece, including its protrusions, from a mold. For present purposes, thermoplastic resin is a resin that softens when heated and hardens again when cooled. Thermosetting resin is a resin that hardens when heated, cannot be remolded and is deformable from a solid to a liquid. Curable resins are resins that are toughened or hardened by cross-linking of their polymer chains, brought about by chemical additives, ultraviolet radiation, electron beam, and/or heat.

In yet another embodiment, the resin comprises at least one polymer having a Young's modulus of greater than 17 MPa.

In still yet another embodiment, the resin comprises at least one polymer having a Young's modulus ranging from 20 MPa to 5 GPa.

In yet still another embodiment, the polymer is selected from at least one of a thermoplastic polymer. For present purposes, thermoplastic polymer is a polymer that softens when heated and hardens again when cooled.

In another embodiment, the polymer is selected from at least one of poly(lactic-co-glycolic acid) (PLGA), polylactic acid (PLA), polydioxanone (PDO), poly(trimethylene carbonate), poly(caprolactone-co-glycolide) and polypropylene (PP).

In still another embodiment, the resin is hydrophobic. For present purposes, a hydrophobic resin is a resin that does not substantially absorb, or be wetted by, water.

In yet another embodiment, the resin is hydrophobic and comprises a polymer selected from aliphatic polyesters, and polypropylenes.

In still yet another embodiment, the resin is hydrophilic. For present purposes, hydrophilic resins are resins that have a Young's modulus greater than 17 MPa and can be generally classified by their interaction with water into roughly two types, water-soluble resins and water-absorbent resins. Water-soluble resins are hydrophilic resins of the type which dissolve in water and are used, for example, as water treatment grade flocculants, oil drilling additives, food additives, and viscosity enhancers. Absorbent resins are water-insoluble hydrophilic resins of the type which absorb water and consequently undergo gelation and are widely used in the fields of agriculture and forestry and in the field of civil engineering as well as in the field of hygienic materials such as disposable diapers and sanitary napkins. In yet still another embodiment, the hydrophilic resin comprises a polymer selected from polyoxaesters, hyaluronic acids, and polyvinyl alcohols.

In another embodiment, the polymer is a biodegradable polymer. For present purposes, a biodegradable polymer is a polymer capable of being decomposed by the action of biological agents, e.g., bacteria, enzymes or water.

In still another embodiment, the polymer is a biodegradable polymer selected from aliphatic polyesters, poly (amino acids), copoly (ether-esters), polyalkylenes oxalates, tyrosine-derived polycarbonates, poly (iminocarbonates), polyorthoesters, polyoxaesters, polyamidoesters, polyoxaesters containing amine groups, poly (anhydrides), polyphosphazenes, collagen, elastin, hyaluronic acid, laminin, gelatin, keratin, chondroitin sulfate, polyglycolide (PGA), poly(propylenefumarate), poly(cyanoacrylate), polycaprolactone (Pa), poly(trimethylene carbonate), poly(lactide), poly(dioxanone), poly(glycerol sebacate) (PGS), poly(glycerol sebacate acrylate) (PGSA), and biodegradable polyurethanes.

In yet another embodiment, the polymer is a non-biodegradable polymer. For present purposes, a non-biodegradable polymer is a polymer that is not capable of being decomposed by the action of biological agents, e.g., bacteria, enzymes, or water.

In still yet another embodiment, the polymer is a non-biodegradable polymer selected from acrylics, polyamide-imide (PAI), polyetherketones (PEEK), polycarbonate, polyethylenes (PE), polybutylene terephthalates (PBT), polyethylene terephthalates (PET), polypropylene, polyamide (PA), polyvinylidene fluoride (PVDF), and polyvinylidene fluoride-co-hexafluoropropylene (PVDF/HFP), polymethylmethacrylate (PMMA), polyvinylalcohol (PVA), polyhydroxyethylmethacrylate, polyvinylalcohol (PVA), polyhydroxyethylmethacrylate (PHEMA), poly(N-isopropylacrylamide) (PNIPAAm), and polyolefins.

In yet still another embodiment, the adhesive structure surface is substantially planar and the protrusions are within ±45 degrees of normal to the planar surface.

In still yet another embodiment, the adhesive structure surface is substantially planar and the protrusions are within ±30 degrees of normal to the planar surface In another embodiment, the adhesive structure has a protrusion density of from $1\times10^5$ to $6\times10^8$ protrusions/cm$^2$. For present purposes, "protrusion density" can be described as the number of protrusions or pillars present per square centimeter of adhesive structure surface.

In still another embodiment, the adhesive structure has a density of protrusions on its surface ranging from about $10\times10^6$ to about $50\times10^6$ protrusions per cm$^2$.

In yet another embodiment, at least a portion of the adhesive structure has a dry adhesive strength of at least 3 N/cm$^2$ of projected area when measured according to ASTM standard D4501.

In still yet another embodiment, at least a portion of the adhesive structure has a wet adhesive strength of at least 0.5 N/cm$^2$ of projected area when measured according to ASTM standard D4501.

In yet still another embodiment, the polymer is selected from at least one of poly(lactic-co-glycolic acid) (PLGA), polylactic acid (PLA), polydioxanone (PDO), poly(glycolide), poly(trimethylene carbonate), poly(glycolide) and polypropylene (PP) and adhesion is measured by adhesive force measurements and ranges from 0.1 to 0.5 N/cm$^2$ on a target surface having a roughness of 0.1 to 8 microns.

In another embodiment, the adhesive structure is at least partially formed by a process selected from nano-molding using a template, polymer self-assembly, lithography, and etching.

The surgical mesh to which the adhesive structure is laminated may be one as described in U.S. Pat. No. 6,638,284, incorporated by reference herein in its entirety. It is desirable for a surgical mesh fabric to exhibit certain properties and characteristics. In particular, the mesh should have a burst strength sufficient to ensure that the mesh does not break or tear after insertion into a patient. The mesh should also have a pore size that enables easy visualization of structures through the mesh, minimize camera light reflection and provide a density of crossing fibers sufficient to facilitate fastening in an endoscopic environment. In addition, the construction of the mesh should provide the maximum burst resistance while minimizing foreign body mass and enhancing fabric pliability.

The surgical mesh is preferably fabricated from a yarn that is biocompatible. Preferred are yarns that have already been accepted for use as a suture material. Numerous biocompatible absorbable and non-absorbable yarns can be used to make the surgical meshes described hereinafter.

Suitable non-absorbable materials for use in the present invention include, but are not limited to, cotton, linen, silk, polyamides (polyhexamethylene adipamide (nylon-66), polyhexamethylene sebacamide (nylon-610), polycapramide (nylon-6), polydodecanamide (nylon-12) and polyhexamethylene isophthalamide (nylon-61) copolymers and blends thereof), polyesters (e.g. polyethylene terephthalate, polybutyl terephthalate, copolymers and blends thereof), fluoropolymers (e.g. polytetrafluoroethylene, expanded polytetrafluoroethylene and polyvinylidene fluoride), polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557, 264 issued Dec. 10, 1985 assigned to Ethicon, Inc. hereby incorporated by reference)) and combinations thereof.

The preferred polypropylene yarns for the present invention utilizes as the raw material pellets of isotactic polypropylene homopolymer having a weight average molecular weight of from about 260,000 to about 420,000. Polypropylene of the desired grade is commercially available in both powder and pellet form.

Suitable absorbable (or biodegradable) materials for use as yarns include but are not limited to aliphatic polyesters which include but are not limited to homopolymers and copolymers of lactide (which includes lactic acid d-,l- and meso-lactide), glycolide (including glycolic acid), c-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, c-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Fibers and/or yarns may be made from absorbable and non-absorbable materials described above in heterologous yarns or bicomponent yarns. Additionally, fibers with different materials used in the sheath and core may also be used for the surgical meshes.

In a preferred embodiment, the surgical mesh is fabricated from a monofilament yarn formed from a polypropylene resin, such as that disclosed in U.S. Pat. No. 4,911,165, entitled "Pliablized Polypropylene Surgical Filaments" and assigned to Ethicon, Inc., the contents of which is hereby incorporated in its entirety by reference. The preferred monofilament polypropylene yarn used has a diameter of from about 3.0 to about 6.0 mils, and more preferably a diameter of about 3.5 mils. Alternatively, a multifilament yarn, such as a multifilament polypropylene yarn may be used to fabricate a surgical mesh in accordance with the present invention.

The surgical mesh can be a woven fabric, a knitted fabric, a nonwoven fabric or even in the form of a porous film, such as an expanded polytetrafluoroethylene film.

As earlier noted, in another aspect the present invention relates to an adhesive structure comprising a two-sided substrate from each side of which extend protrusions comprising one or more resins having a Young's modulus of greater than 17 MPa, which protrusions are of sufficiently low diameter to promote adhesion by increasing physical attractive forces between the adhesive structure and a target surface, as measured by shear adhesion.

In one embodiment of this aspect, the protrusions have an average diameter ranging from 0.2 to 5 microns, an average length greater than 1 micron and an aspect ratio (length/diameter) of 1 to 33.

In another embodiment, the protrusions have an average diameter ranging from 0.2 to 2 microns, an average length greater than 3 microns and an aspect ratio (length/diameter) of 2 to 30.

In still another embodiment, the adhesive structure is integrally molded from a resin selected from at least one of thermoplastic resin, thermosetting resin, and curable resin.

In yet another embodiment, the resin comprises at least one polymer having a Young's modulus of greater than 17 MPa.

In still yet another embodiment, the resin comprises at least one polymer having a Young's modulus ranging from 20 MPa to 5 GPa.

In yet still another embodiment, the polymer is selected from at least one of a thermoplastic polymer.

In another embodiment, the polymer is selected from at least one of poly(lactic-co-glycolic acid) (PLGA), polylactic acid (PLA), polydioxanone (PDO), poly(trimethylene carbonate), poly(caprolactone-co-glycolide) and polypropylene (PP).

In still another embodiment, the resin is hydrophobic.

In yet another embodiment, the resin is hydrophobic and comprises a polymer selected from aliphatic polyesters, and polypropylenes.

In still yet another embodiment, the resin is hydrophilic.

In yet still another embodiment, the hydrophilic resin comprises a polymer selected from polyoxaesters, hyaluronic acids, and polyvinyl alcohols.

In another embodiment, the polymer is a biodegradable polymer.

In still another embodiment, the polymer is a biodegradable polymer selected from aliphatic polyesters, poly (amino acids), copoly (ether-esters), polyalkylenes oxalates, tyrosine-derived polycarbonates, poly (iminocarbonates), polyorthoesters, polyoxaesters, polyamidoesters, polyoxaesters containing amine groups, poly (anhydrides), polyphosphazenes, collagen, elastin, hyaluronic acid, laminin, gelatin, keratin, chondroitin sulfate, polyglycolide (PGA), poly(propylenefumarate), poly(cyanoacrylate), polycaprolactone (Pa), poly(trimethyene carbonate), poly(lactide), poly(dioxanone), poly(glycerol sebacate) (PGS), poly(glycerol sebacate acrylate) (PGSA), and biodegradable polyurethanes.

In yet another embodiment, the polymer is a non-biodegradable polymer.

In still yet another embodiment, the polymer is a non-biodegradable polymer selected from acrylics, polyamide-imide (PAI), polyetherketones (PEEK), polycarbonate, polyethylenes (PE), polybutylene terephthalates (PBT), polyethylene terephthalates (PET), polypropylene, polyamide (PA), polyvinylidene fluoride (PVDF), and polyvinylidene fluoride-co-hexafluoropropylene (PVDF/HFP), polymethylmethacrylate (PMMA), polyvinylalcohol (PVA), polyhydroxyethylmethacrylate, polyvinylalcohol (PVA), polyhydroxyethylmethacrylate (PHEMA), poly(N-isopropylacrylamide) (PNIPAAm), and polyolefins.

In yet still another embodiment, the adhesive structure surface is substantially planar and the protrusions are within ±45 degrees of normal to the planar surface.

In another embodiment, the adhesive structure has a protrusion density of from $1\times10^5$ to $6\times10^8$ protrusions/cm$^2$.

In yet another embodiment, at least a portion of the adhesive structure has a dry adhesive strength of at least 3 N/cm$^2$ of projected area when measured according to ASTM standard D4501.

In still yet another embodiment, at least a portion of the adhesive structure has a wet adhesive strength of at least 0.5 N/cm$^2$ of projected area when measured according to ASTM standard D4501.

In yet still another embodiment, the adhesive structure polymer is selected from at least one of poly(lactic-co-glycolic acid) (PLGA), polylactic acid (PLA), polydioxanone (PDO), poly(glycolide), poly(trimethylene carbonate), poly (glycolide) and polypropylene (PP) and adhesion is measured by adhesive force measurements and ranges from 0.1 to 0.5 N/cm$^2$ on a target surface having a roughness of 0.1 to 8 microns.

In another embodiment, the adhesive structure is at least partially formed by a process selected from nanomolding using a template, polymer self-assembly, lithography, and etching.

In yet another embodiment, the two-sided substrate comprises one or more extruded resin layers.

In still another embodiment, the adhesive structure two-sided substrate comprises two or more co-extruded resin layers, each of which resin layer can be the same as or different from another resin layer of the substrate.

In still yet another embodiment, the two-sided substrate is derived from a film co-extruded from more than one resin.

In yet still another embodiment, the two-sided substrate is selected from a single layer substrate comprising the adhesive structure described above, a double layer substrate comprising a surgical mesh core layer and an adhesive structure skin layer, and a triple layer substrate having a surgical mesh core layer and two adhesive structure skin layers.

As earlier noted, in another aspect, the present invention relates to a laminate of a surgical mesh and an adhesive structure comprising a surface from which extend protrusions comprising a resin having a Young's modulus of greater than 17 MPa, which protrusions are of sufficiently low diameter to promote adhesion by increasing physical attractive forces, as measured by shear adhesion, between the adhesive structure and a target surface, said adhesive structure further comprising chemical groups on at least a portion of the adhesive structure surface, capable of interacting with the target surface.

In an embodiment of this aspect of the invention, the chemical groups are provided by cyanoacrylates, fibrin sealants, hydroxysuccinimides, acrylates, and aldehydes.

In another embodiment of this aspect of the invention, the chemical groups are provided by fibrin sealants.

In another embodiment, the protrusions have an average diameter ranging from 0.2 to 2 microns, an average length greater than 3 microns and an aspect ratio (length/diameter) of 2 to 30.

In still another embodiment, the structure is integrally molded from a resin selected from at least one of thermoplastic resin, thermosetting resin, and curable resin.

In yet another embodiment, the resin comprises at least one polymer having a Young's modulus of greater than 17 MPa.

In still yet another embodiment, the resin comprises at least one polymer having a Young's modulus ranging from 20 MPa to 5 GPa.

In yet still another embodiment, the polymer is selected from at least one of a thermoplastic polymer.

In another embodiment, the polymer is selected from at least one of poly(lactic-co-glycolic acid) (PLGA), polylactic acid (PLA), polydioxanone (PDO), poly(trimethylene carbonate), poly(caprolactone-co-glycolide) and polypropylene (PP).

In still another embodiment, the resin is hydrophobic.

In yet another embodiment, the resin is hydrophobic and comprises a polymer selected from aliphatic polyesters, and polypropylenes.

In still yet another embodiment, the resin is hydrophilic.

In yet still another embodiment, the hydrophilic resin comprises a polymer selected from polyoxaesters, hyaluronic acids, and polyvinyl alcohols.

In still another embodiment, the polymer is a biodegradable polymer selected from aliphatic polyesters, poly (amino acids), copoly(ether-esters), polyalkylenes oxalates, tyrosine-derived polycarbonates, poly (iminocarbonates), polyorthoesters, polyoxaesters, polyamidoesters, polyoxaesters containing amine groups, poly (anhydrides), polyphosphazenes, collagen, elastin, hyaluronic acid, laminin, gelatin, keratin, chondroitin sulfate, polyglycolide (PGA), poly(propylenefumarate), poly(cyanoacrylate), polycaprolactone (PCL), poly(trimethylene carbonate), poly(lactide), poly(dioxanone), poly(glycerol sebacate) (PGS), poly(glycerol sebacate acrylate) (PGSA), and biodegradable polyurethanes.

In still yet another embodiment, the polymer is a non-biodegradable polymer selected from acrylics, polyamide-imide (PAI), polyetherketones (PEEK), polycarbonate, polyethylenes (PE), polybutylene terephthalates (PBT), polyethylene terephthalates (PET), polypropylene, polyamide (PA), polyvinylidene fluoride (PVDF), and polyvinylidene fluoride-co-hexafluoropropylene (PVDF/HFP), polymethylmethacrylate (PMMA), polyvinylalcohol (PVA), polyhydroxyethylmethacrylate, polyvinylalcohol (PVA), polyhydroxyethylmethacrylate (PHEMA), poly(N-isopropylacrylamide) (PNIPAAm), and polyolefins.

In yet still another embodiment, the adhesive structure surface is substantially planar and the protrusions are within +45 degrees of normal to the planar surface.

In another embodiment, the adhesive structure has a protrusion density of from $1\times10^5$ to $6\times10^8$ protrusions/cm$^2$.

In yet another embodiment, at least a portion of the adhesive structure has a dry adhesive strength of at least 3 N/cm$^2$ of projected area when measured according to ASTM standard D4501.

In still yet another embodiment, at least a portion of the adhesive structure has a wet adhesive strength of at least 0.5 N/cm$^2$ of projected area when measured according to ASTM standard D4501.

In yet still another embodiment, the polymer is selected from at least one of poly(lactic-co-glycolic acid) (PLGA), polylactic acid (PLA), polydioxanone (PDO), poly(glycolide), poly(trimethylene carbonate), poly(glycolide) and polypropylene (PP) and adhesion is measured by adhesive force measurements and ranges from 0.1 to 0.5 N/cm$^2$ on a target surface having a roughness of 0.1 to 8 microns.

In another embodiment, the adhesive structure is at least partially formed by a process selected from nano-molding using a template, polymer self-assembly, lithography, and etching.

In still another embodiment, the adhesive structure comprises a two-sided substrate from each side of which extend the protrusions.

In yet another embodiment, the two-sided substrate comprises one or more extruded resin layers.

In still another embodiment, the two-sided substrate comprises two or more co-extruded resin layers, each of which resin layer can be the same as or different from another resin layer of the substrate.

In still yet another embodiment, the two-sided substrate is derived from a film co-extruded from more than one resin.

In another embodiment of this aspect, the chemical groups are selected from pressure sensitive adhesives such as acrylates, adhesives applied in the molten state (hot melt adhesives), solvent based adhesives such as poly(vinyl acetate), multi-part adhesives that can be cured by radiation, heat or moisture such as cyanoacrylates, and urethanes, natural sealants such as fibrin sealants and starches, hydroxysuccinimides, and aldehydes.

As earlier noted, another aspect of the invention is directed to a method of providing an adhesive structure adherable to a target surface which comprises: a) measuring surface roughness of the target surface to determine the average longest dimension of microstructures associated with the surface roughness; b) forming a polymer-containing adhesive structure comprising an adhesive surface which includes protrusions of a sufficiently low average diameter to interact with target microstructures on the target surface to promote adhesion by increasing physical attractive forces between the adhesive structure and the target surface, as measured by shear adhesion; and c) laminating a surgical mesh to a non-adhesive surface of said adhesive structure.

In one embodiment, the polymer has a Young's modulus above 17 MPa.

In another embodiment, the target surface comprises biological tissue.

In still another embodiment, the target surface is selected from at least one of bladder tissue and intestinal tissue.

As earlier noted, yet another aspect of the invention relates to a method for preparing an adhesive structure which comprises: a) providing a specific solvent-dissolvable mold including indentations; b) providing a meltable polymer having a Young's modulus of greater than 17 MPa to the mold under conditions sufficient to permit filling the indentations of the mold by the polymer, said polymer being substantially non-dissolvable by the specific solvent; c) treating the mold and polymer of step b) to an extent sufficient to substantially solidify the polymer; d) laminating a surgical mesh, also non-dissolvable by said specific solvent, to the exposed surface of said meltable polymer at the top of said mold; and e) exposing the mold, polymer and surgical mesh to the specific solvent under mold-dissolving conditions to provide a surgical mesh/molded polymer substrate material having a Young's modulus of greater than 17 MPa comprising protrusions conforming to the indentations of the mold. Optionally, this aspect further comprises at least one of the following conditions:

i) wherein the meltable polymer is provided to the mold as a softened film;
ii) wherein the mold comprises polycarbonate, the polymer is thermoplastic, meltable polymer, e.g., polydioxanone and the solvent is dichloromethane; and
iii) wherein step b) is carried out in a first stage and second stage, wherein the second stage is carried out at a greater pressure.

For present purposes, a meltable polymer can include a single polymer or a mixture of polymers.

In one embodiment, the first stage is carried out at a temperature ranging from 90 to 110° C., pressure ranging from about 0 to about 20 kPa (about 0 to about 20 Bar), for a duration of 7 to 12 minutes, and the second stage is carried out at a temperature ranging from 90 to 110° C., pressure ranging from about 6 to about 20 kPa (about 6 to about 20 Bar), for a duration of 15 to 25 minutes.

In yet another embodiment, step b)'s conditions are sufficient to permit filling the indentations of the mold by the polymer and include pressures provided by upper and lower horizontal opposing surfaces, between which surfaces is positioned a space-filling shim surrounding an opening in which are placed from the bottom 1) a first solvent-dissolvable mold layer, 2) a first meltable polymer layer, 3) a surgical mesh layer, 4) a second meltable polymer layer, and 5) a second solvent-dissolvable mold layer, and further wherein, 6) an optional protective layer is provided between the lower horizontal opposing surface and the first solvent-dissolvable mold layer and 7) an optional protective layer is provided between the upper horizontal opposing surface and the second solvent-dissolvable mold layer.

In a particularly advantageous embodiment, the laminate further comprises an adhesion barrier on the side of the surgical mesh opposite the adhesive structure. Adhesion barriers are designed to inhibit post surgical adhesions from forming between adjacent tissues and/or organs, while the patient is recovering and healing from the surgery, and while new tissue is forming within the pores of the porous basic structure.

Suitable adhesion barriers for use with the present invention include, but are not limited to oxidized regenerated cellulose (e.g., INTERCEED absorbable adhesion barrier), polymeric films (e.g., MONOCRYL material), SupraSeal, adhesion barriers consisting of D,L-polylactide (PDLA-Copolymer), SurgiWrap (MAST Biosurgery, San Diego, Calif.)

Adhesion Barrier Film made of polylactide (PLA), polyoxaesters (U.S. Pat. No. 6,403,655—incorporated by reference herein in its entirety), PEDG (U.S. Pat. No. 7,754,233—incorporated by reference herein in its entirety), enteric carrier materials (U.S. Patent Publication No. US 2009/0318843—incorporated by reference herein in its entirety), hydrogel films or coatings that are biocompatible (e.g., ETHICON INTERCOAT™ Absorbable Adhesion Barrier Gel, SprayGel® Adhesion Barrier (Confluent Surgical, Waltham, Mass.) and Adhibit™ adhesion prevention gel (Angiotech Pharmaceuticals Inc., Vancouver, BC)—both polyethylene glycol-based precursor liquids, which rapidly cross-link on the target tissue to form a flexible, adherent, bioabsorbable gel barrier); Oxiplex®, Oxiplex®/SP and MediShield™ (flowable gel made of carboxymethylcellulose and polyethylene oxide), CoSeal Adhesion Prevention Products (polyethylene glycol polymer), Teflon PTFE materials (e.g., Gor-tex Surgical Membrane (W.L. Gore & Associates, Inc., Flagstaff, Ariz.), sodium hyaluronate based materials (e.g., ACP gel (Baxter, Italy); SEPRAFILM adhesion barrier from Genzyme (modified hyaluronic acid and carboxymethylcellulose—forms a hydrophilic gel); INTERGEL adhesion prevention solution, and biologics such as fibrinolytic agents (e.g., recombinant human tissue plasminogen activator (rt-PA)) and fibrin glues.

The invention is further explained in the description that follows with reference to the drawings illustrating, by way of non-limiting examples, various embodiments of the invention.

Example 1

The aim of this example was to fabricate polypropylene films with pillar like protrusions. A commercial track etched polycarbonate membrane was obtained from Millipore Corporation of Billerica, Mass., USA having pores of 0.6 microns diameter and a circular diameter of 2.5 cm, with a thickness of 20 microns. The membrane was used as a template to imprint a solvent-resistant polypropylene (PP) polymer film of 300 microns thickness, obtained from Ethicon, Inc. of Somerville, N.J., USA. The polypropylene film was pressed into the polycarbonate membrane template under controlled temperature and pressures (180° C., 600 kPa (6 bar)) for 20 minutes, melting the polypropylene and forming an overfilling of polypropylene to the top side of the membrane. The polypropylene polymer and the membrane are cooled to 175° C. before removal of pressure, after which the polymer structures are de-molded and released by dissolving the membrane in dichloromethane. The overfilling of polypropylene holds the resulting pillar-like structures in place in the subsequent removal of the membrane by dissolving with dicholoromethane. After the membrane was completely dissolved and dried, the substrate was exposed to oxygen plasma to etch the overfilled layer of polymer on top, thereby releasing the pillar-like structures. FIG. 1 depicts a scanning electron microscope image of the resulting polypropylene substrate with micropillars (substantially cylindrical protrusions) of 0.6 microns diameter×20 microns length.

Example 2

The aim of this example was to develop an accurate and reproducible test method to measure shear adhesion. Modifications were made to the mechanical testing instrument sold under the trade name INSTRON by Instron Industrial Products, Grove City, Pa. The mechanical testing set up was modified to improve the precision and reproducibility of the shear adhesion measurements of the films having pillar-like structures. The modifications were made to decrease the source of noise from the hardware components and control the preload or initial contact force between the adhesive surfaces. The standard clamp operated with compressed air to grip the glass slide was replaced by a fixed rigid clamp and the length of the glass slide was shortened to reduce noise due to cantilever bending effect. Similarly, the length of the lower glass slide was shortened to reduce noise. A solid block of aluminum was used as a backing for the glass slide. A control of preload was added consisting of: a spring gauge to the preload force between the surfaces. The spring gauge consisted of a spring that is translated to distance when a force is applied. The spring constant was measured and 20 mN of load translated to 10 units on the dial. As the spring constant was linear, the amount of preload was varied by reading the displacement of the dial in the gauge. During testing, the spring gauge was first brought in light contact with the upper glass slide. Using the XY stage, the lower glass slide was brought in contact with the upper glass slide and a displacement shown on the dial. For all the tests, 30 mN of preload was set (literature values vary from 20-40 mN). After the preload was set, the spring gauge was removed to prevent noise from the spring when the tester was in motion. With the rigid upper clamp, preload was constant throughout the duration of the tests, maintaining a constant preload value from sample to sample to compare adhesion values.

Example 3

Figure 2:
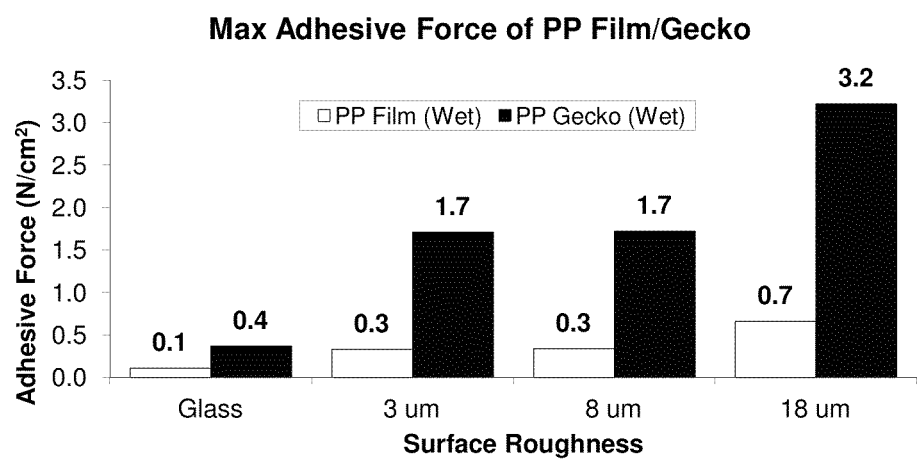
FIG. 2 presents shear adhesion forces (adhesive forces) between polypropylene substrates with pillar-like extensions of 1 micron diameter and 20 microns length and target substrates of varying surface roughness values—flat glass, 3 microns, 8 microns, and 18 microns, under wet conditions i.e. when immersed in a water bath.

The polypropylene pillared substrate prepared as described in Example 1 as well as its corresponding flat surface film (unpillared) were tested for shear adhesion against substrates (sandpaper) with varying surface roughness values under wet conditions i.e. the substrates and the structures were immersed in DI water and the mechanical testing was then conducted by the method described in Example 2. This was done to mimic the wet conditions that exist in-vivo. The surface roughness value represents the average feature dimensions expected for different surfaces. These tests were performed using a mechanical tester sold under the trade name INSTRON (Instron Industrial Products, Grove City, Pa.) and the results are summarized in FIG. 2. The results clearly show that the flat, unpatterned PP films show uniformly low adhesion over all substrate roughnesses. The adhesion of the PP nanopillars (1 micron diameter and 20 microns length) was higher than its flat counterpart, as well as being a function of the substrate roughness. Maximum adhesive force was seen on a substrate roughness of 18 microns.

From this data we have shown that the dimensions of the pillar-like protrusions need to be tailored to match the substrate roughness for maximum adhesion.

Example 4

Figure 3:
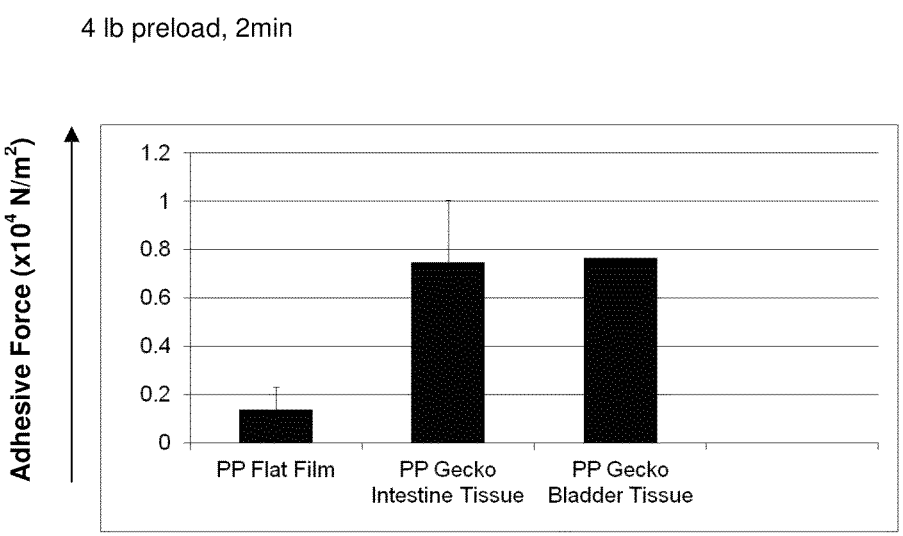
FIG. 3 depicts shear adhesion force ($10^4$ N/m$^2$) comparisons for polypropylene substrates with pillar-like extensions of 1 micron diameter and 20 micron length and target substrates against flat PP film and two tissue types—intestine and bladder.

The polypropylene pillared substrate prepared as described in Example 1 as well as its corresponding flat surface film (unpillared) were tested against, two tissue types, porcine intestine and porcine bladder for tissue adhesion using the methods described in Example 5. Adhesive force was measured with a 1.8 kg (four pound) preload for two minutes. These tissues differ in characteristics such as elasticity, thickness, and surface roughness. The shear adhesion data is shown in FIG. 3. The PP film with 1 micron×20 microns pillar-like protrusions can be used with different tissues. The corresponding polypropylene flat film provided about $0.14 \times 10^4$ N/m² adhesive force. Intestine tissue provided about 0.75×10⁴ N/m² adhesive force, while the bladder tissue provided about 0.78×10⁴ N/m² adhesive force.

Example 5

Ex-Vivo Tissue Adhesion Tests

Figure 4:
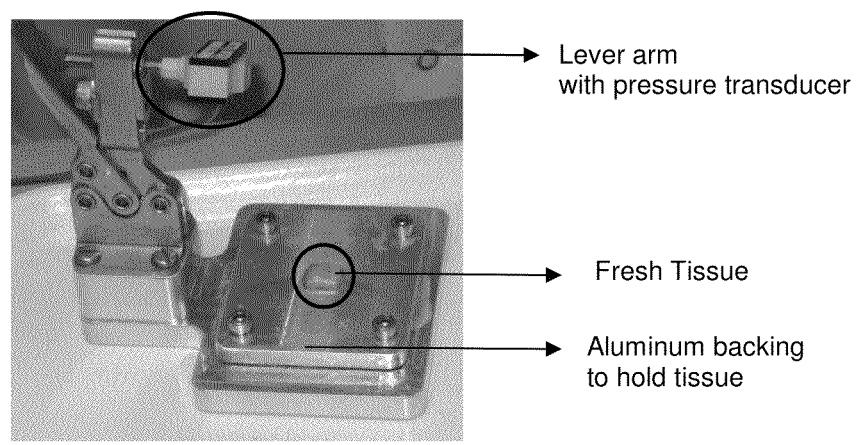
FIG. 4 is a photograph depicting a sample holder apparatus used to hold tissue samples when measuring shear adhesion of polymer samples to freshly harvested tissue on a mechanical testing set-up.
Figure 5:
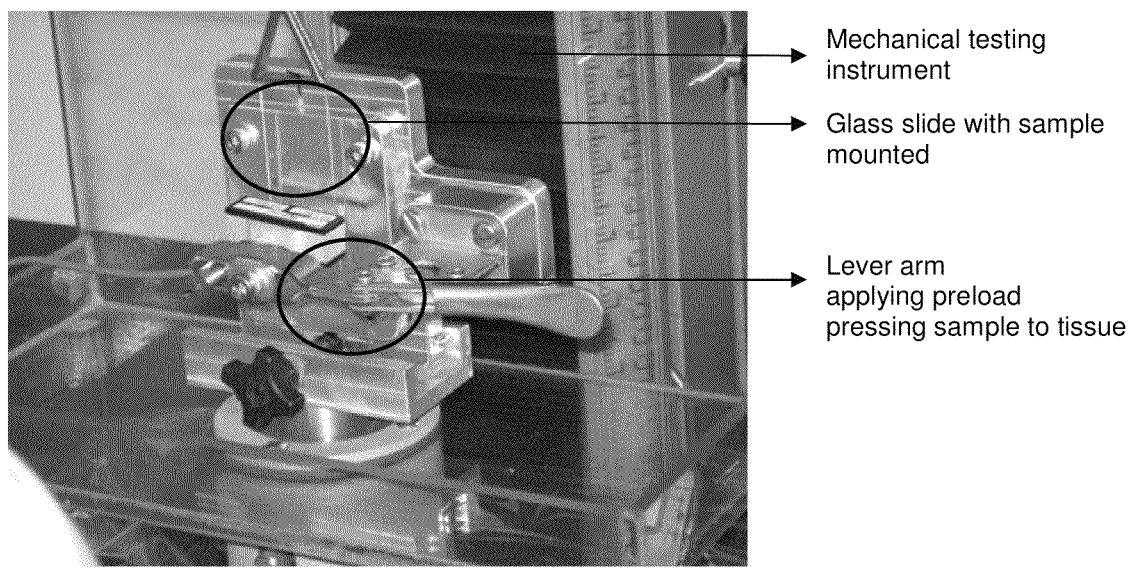
FIG. 5 is a photograph depicting a sample holder apparatus for a tissue sample mounted on a mechanical tester for measuring shear adhesion of polymer samples to freshly harvested tissue.

The aim of this example was to develop an accurate and reproducible test method to measure shear adhesion to tissue samples. Shear adhesion values of polypropylene samples of the present invention against freshly harvested tissue were measured on a mechanical testing instrument sold under the trade name INSTRON by Instron Industrial Products, Grove City, Pa. The polymer sample was made on a polymer substrate and the fresh tissue was soft and flexible. The tissue was mounted in the apparatus shown in FIG. 4 which comprises a lever arm to press the tissue against the polymer sample, a pressure transducer to measure pressures generated by the lever arm and a rigid aluminum backing to provide support for the soft and flexible tissue to which the tissue was secured to prevent slippage during the testing process. This also provided a known contact area of the sample with the tissue. The aluminum holder was then vertically mounted on the mechanical tester as shown in FIG. 5. The polymer sample was mounted on a glass slide using double sided tape. The glass slide with the sample was then mounted on the mechanical tester, and its height was adjusted so that the polymer sample lined up with the exposed tissue area. The sample was then gently pressed onto the tissue surface. The lever arm was then lowered to bring the pressure transducer in contact with the back of the glass slide. The screw on the lever arm was used to tighten the glass slide with the substrate mounted against the tissue as shown in FIG. 5. This was the preload force and could be read on a digital readout attached to the pressure transducer. This preload was applied for a specific amount of time with the preload force of about four pounds and time of about 120 seconds intended to simulate a person applying a tape or a skin adhesive bandage.

After the appropriate amount of time, the preload force was removed by pulling back on the lever arm. The load as read by the mechanical tester was zeroed and test was then commenced. For the test method, the glass slide was pulled upwards at the rate of 8 mm/min and the force was recorded. The maximum force was then recorded as a measure of the shear adhesive force.

Example 6

Figure 6:
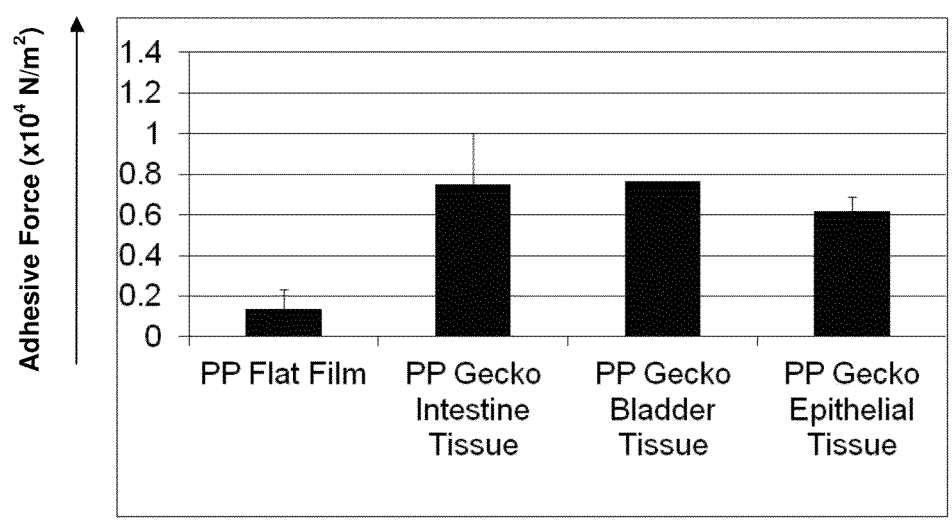
FIG. 6 depicts adhesion strength for a polypropylene substrate of the present invention having pillars of about one micron diameter and about 20 microns in length against three different tissue types—intestine, bladder, and epithelium.

The polypropylene samples prepared as described in Example 1 were tested for tissue adhesion against three tissue types i.e. intestine, bladder and epithelium, using the methods described in Example 5. The results are shown in FIG. 6. The polypropylene protrusions or pillars were about one micron in diameter and about 20 microns in length (height) and the intestine and bladder tissues were smoother than the epithelial tissue which was determined to have surface roughness of about 5.6 microns to 12 microns as determined using a surface profiler (NT 9100, Veeco Instruments Inc, Plainview, N.Y.). The dimensions of the polypropylene protrusions or pillars appear closer to the surface roughness of the intestine and bladder tissues, which were determined to have surface roughnesses of about 0.3 micron to about 1.85 microns and from about 0.75 micron to about 2.8 microns, respectively. Consequently, the adhesion values were higher. This behavior was consistent with the effect seen on adhesion to substrates with defined roughnesses.

Example 7

Figure 7:
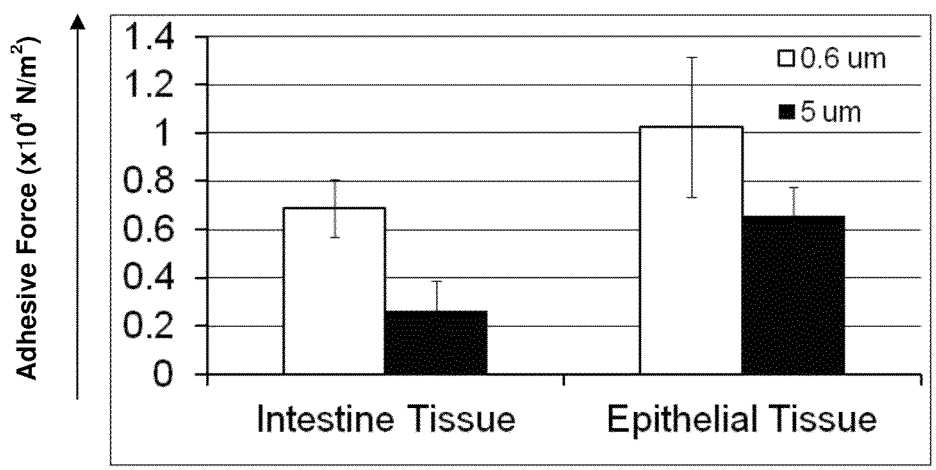
FIG. 7 depicts the effect of pillar dimensions of polypropylene substrates having respective pillar dimensions of about 0.6 micron diameter×about 20 microns lengths and 5 microns diameter×about 15 microns lengths when tested against two tissue types, intestine and epithelium.
Figure 8:
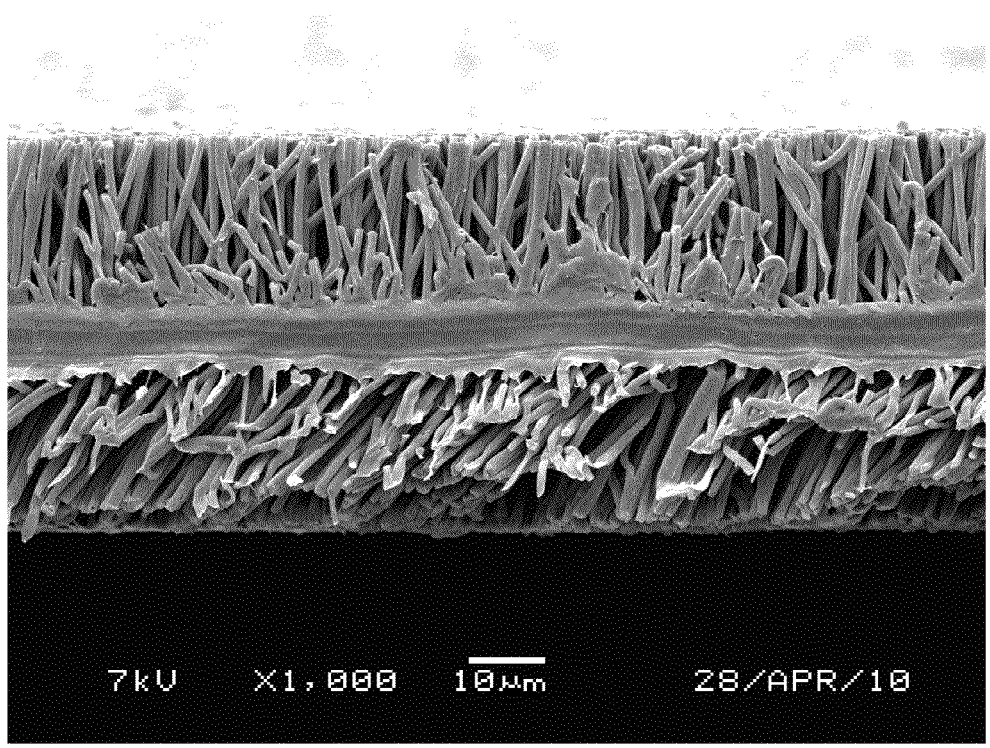
FIG. 8 depicts a SEM image of a polypropylene tape with adhesive features on both sides.
Figure 9:
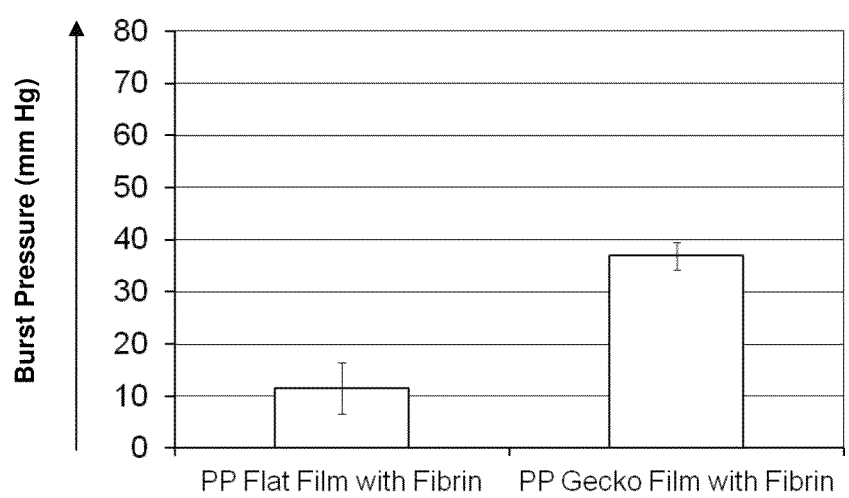
FIG. 9 depicts the comparison of the burst pressure data for a flat PP film and the double sided PP tape on a porcine intestine.

In order to determine the effect of pillar dimensions, polypropylene samples with different pillar dimensions (about 0.6 micron diameter×about 20 microns length and about 5 microns diameter×about 15 microns length) prepared as in Example 1 were tested against two tissue types, i.e., intestine and epithelium, as described in Example 5. As mentioned earlier, the intestine tissue was smoother than the epithelial tissue. From the results shown in FIG. 7, it can be seen that the smaller diameter pillars show enhanced adhesion to both tissue types. However, adhesion on the intestine tissue using the 0.6 micron pillars is 2.6 times the adhesion of the bigger five microns pillars. Adhesion on the epithelial tissue using the 0.6 micron pillars is only 1.5 times the adhesion of the bigger 5 microns pillars. This indicates that the adhesion enhancement using the smaller diameter, but taller pillars was greater on the smoother tissue type. Thus the trend of using nanopillars matching the roughness of the tissue for enhanced adhesion can be seen in this example.

Example 8

An experiment was conducted to prepare a polypropylene film with pillar-like structures on both sides and test its effectiveness for adhesion to tissue. The polypropylene film with pillar-like structures on both sides were prepared as follows: A 25 microns thick polypropylene film was compressed under heat and pressure between two 20 microns thick sheets of polycarbonate filter material, which polycarbonate filter material thickness corresponds to the desired length (or height) of the pillar-like structures to be formed. The filter material possessed microscopic (0.8 micron) holes, which correspond to the eventual diameter of the pillar-like structures to be formed. The polypropylene film melted and flowed into the holes. After processing, the sheet was annealed. The polycarbonate membrane filter was then dissolved in a bath of dichloromethane. The membrane filters (0.8 micron ATTP, Cat No. ATTP14250, Lot No. R9SN70958, available from Millipore Corporation of Billerica, Mass., USA) possessed two distinct sides, one having a shiny appearance while the other side was duller. A laminate for compression molding was constructed as follows:

a. A segment of polyimide film (sold under the trade name KAPTON by DuPont, Wilmington, Del.) of 65-70 microns thickness, was placed on a table;
b. A 15.2 cm (6 inch) polished square metal plate (thickness 0.8 mm) was placed (shiny side up) on the polyimide film;
c. A segment of polyimide film was placed on the 15.2 cm (6 inch) plate;
d. A 15.2 cm×15.2 cm (6"×6")×80 microns steel shim with a 10.1 cm×10.1 cm (4"×4") cavity in the center was placed on the polyimide film;
e. A membrane filter was cut to fit in the shim cavity and placed (dull side up) on the polyimide film;
f. A piece of 25 microns thick polypropylene film was cut to fit in the shim cavity and the sample was placed on the membrane;
g. Another membrane filter (about 20 microns thick) was cut to fit in the shim cavity and placed (dull side down) on the polypropylene film;
h. A segment of polyimide film was placed on the top membrane;
i. A 15.2 cm (6 inch) polished square metal plate (thickness 0.8 mm) (shiny side up) was placed on the polyimide film; and j. Another segment of polyimide film was placed on the steel plate.

Any thermoformable material as previously described can be substituted for polypropylene as the substrate or core material. The porous solvent-dissolvable polycarbonate material which acts as a template for the pillar-like protrusions of the product can be substituted by another solvent-dissolvable porous polymeric material. Alternately, a strippable mold such as anodized aluminum oxide can be substituted to provide the pillar-like cylindrical protrusions of the final product, without the need for exposure to a chemical solvent. Polyimide film was used as a capping means or shield to protect polymer surfaces from directly contacting surfaces such as metal. Other suitable substantially chemically inert materials which can also be provided as a film or other layer for this purpose include polytetrafluoroethylene (sold under the trade name TEFLON by DuPont, Wilmington, Del.). Advantageously, these materials are not reactive with the polycarbonate solvent-dissolvable mold or template material and can be readily removed or peeled therefrom once compression is completed.

The resulting sample was loaded into a heated press with vacuum (less than 150 microns mercury) capability and was processed as follows:
a. Top and bottom platens were preheated to 190° C. (374° F.);
b. The sample was preheated under vacuum for 300 seconds prior to any compression;
c. The sample was compressed at 68948 kPa (10,000 psi) for 300 seconds;
d. Temperature was reduced to 21° C. (70° F.) while maintaining compression of 68948 kPa (10,000 psi);
e. Compressive force was released and vacuum was purged; and
f. The sample was removed from the vacuum press.

The sample was annealed in the constrained condition (between two steel plates) in an oven purged with nitrogen gas at 130° C. immediately for two hours. Temperature was reduced to 100° C. and the sample was annealed at this temperature for an additional 12.5 hours. Finally, the temperature was slowly reduced to 25° C. over a period of five hours. The annealing of the sample was then complete.

The polycarbonate membrane had been fused to the surface of the polypropylene film. The membrane was removed by chemical etching. The membrane was removed from the surface of the polypropylene film by immersing the sample in a bath of dichloromethane at room temperature for five minutes. The resulting sample was allowed to air dry prior to handling. Scanning electron microscope (SEM) images confirmed the presence of pillar-like structures which were about 20 microns high and 0.8 microns in diameter.

In order to assess the capacity of the modified film to promote tissue adhesion, a study was conducted. A 2.5 cm by 10.1 cm (1 inch by 4 inch) section of polypropylene film with pillar structures was cut from the sheet prepared as described above. Another 2.5 cm by 10.1 cm (1 inch by 4 inch) sample of 25 microns thick polypropylene film without pillar structures was used as a control. Fresh porcine small intestine was cleaned with Phosphate Buffered Saline (PBS) at room temperature. A section of the intestine approximately 10.1 cm (4 inches) long was mounted in a fixture that allowed it to be inflated with air and at the same time monitored the air pressure within the intestine. A one centimeter long incision was made in the center of the intestine segment its length. Fibrin sealant (Human), sold under the trade name EVICEL by Johnson & Johnson Wound Management, a division of Ethicon Inc. of Somerville, N.J., USA was prepared in accordance with the manufacturer's directions. The 5 mL application device for the sealant was used to aspirate a coating of fibrin sealant onto the surfaces of both films. The films were then wrapped around the circumference of the intestine covering the 1 cm long incision. The films were then clamped in place with a spring-loaded clamp while the fibrin sealant was allowed to stabilize for 5 minutes. The sample was then immersed in a PBS bath maintained at 37° C. and slowly inflated with air (approximately 5 mm Hg/sec). The air pressure increased until a maximum value was reached at which point air bubbles were observed in the PBS bath. The maximum value achieved by the control film under these conditions was 8.1 mm Hg. The maximum value achieved by the film with the pillar structures under these conditions was 41.6 mm Hg. The film with the pillar structures was thus able to attain a burst pressure greater than five times that of the control in this experiment.

Example 9

A 100 microns thick polydioxanone film with pillar-like structures on both sides was prepared. A polydioxanone film was compressed under heat and pressure between two 20 microns thick sheets of polycarbonate filter material. The filter material possesses microscopic (0.8 micron) holes. The polydioxanone film melted and flowed into the holes. After processing the sheet was annealed. The polycarbonate membrane filter was then dissolved in a bath of dichloromethane. The membrane filters used (0.8 micron ATTP, Cat No. ATTP14250, Lot No. R9SN70958 available from Millipore Corporation of Billerica, Mass., USA) possessed two distinct sides. One side had a shiny appearance while the other was duller. A laminate for compression molding was constructed as follows:
a. A segment of polyimide film (sold under the trade name KAPTON by DuPont, Wilmington, Del.) of 65-70 microns thickness was placed on a table;
b. A 15.2 cm (6 inch) polished square metal plate (thickness 0.8 mm) (shiny side up) was placed on the polyimide film;
c. A segment of polyimide film was placed on the 15.2 cm (6 inch) plate;
d. A 15.2 cm×15.2 cm (6"×6")×80 microns steel shim with a 10.1 cm×10.1 cm (4"×4") cavity in the center was placed on the film;
e. A membrane filter was cut to fit in the shim cavity and was placed (dull side up) on the polyimide film;
f. A piece of 25 microns thick polydioxanone film was cut to fit in the shim cavity. The sample was placed on the membrane;
g. Another membrane filter (about 20 microns thick) was cut to fit in the shim cavity and placed (dull side down) on the polydioxanone film;
h. A segment of polyimide film was placed on the top membrane;
i. A 15.2 cm (6 inch) polished square metal plate (thickness 0.8 mm) (shiny side down) was placed on the polyimide film; and
j. Another segment of polyimide film was placed on the steel plate.

The resulting sample was loaded into a heated press with vacuum (less than 150 microns mercury) capability and was processed as follows:
a. The top and bottom platens were preheated to 220° C. (428° F.);
b. The sample was preheated under vacuum for 300 seconds prior to any compression;

c. The sample was compressed at 68948 kPa (10,000 psi) for 300 seconds;
d. The temperature was reduced to 21° C. (70° F.) while maintaining compression of 68948 kPa (10,000 psi);
e. The compressive force was released and the vacuum was purged; and
f. The sample was removed from the vacuum press.

The sample was annealed in the constrained condition (between two steel plates) in an inert environment (nitrogen gas) for a minimum of six hours at 70° C.

The polycarbonate membrane had been fused to the surface of the polydioxanone film. The membrane was removed by chemical etching. The membrane was removed from the surface of the polydioxanone film by immersing the sample in a bath of dichloromethane at room temperature for five minutes and was allowed to air dry prior to handling. Scanning electron microscope (SEM) images of the sample confirmed the presence of pillar-like structures which were about 20 microns high and 0.8 micron in diameter.

Example 10

An anodized aluminum oxide (AAO) mold was prepared for imprinting of poly(lactic acid) (DL-PLA) polymer into pillar-like structures. The mold was prepared by forming an AAO film by electropolishing and etching, and silane-treating the mold by silane vapor deposition. The resulting mold contains randomly distributed recesses which provide pillar-like projections in the demolded product of 200 nanometers by 2 microns. DL-PLA film obtained from PURAC America of Lincolnshire, Ill., USA and having a thickness of 100-300 microns is pressed into the AAO mold under high temperature and pressure in two steps at 100° C. The first step is carried out at a pressure of 0 kPa (0 bar) for 5 minutes and the second step at 6000 kPa (60 bar) for 20 minutes. The polymer and mold are cooled to 35° C. before removal of pressure. Then, the polymer structures are demolded and released by mechanically peeling them from the mold.

Figure 10:
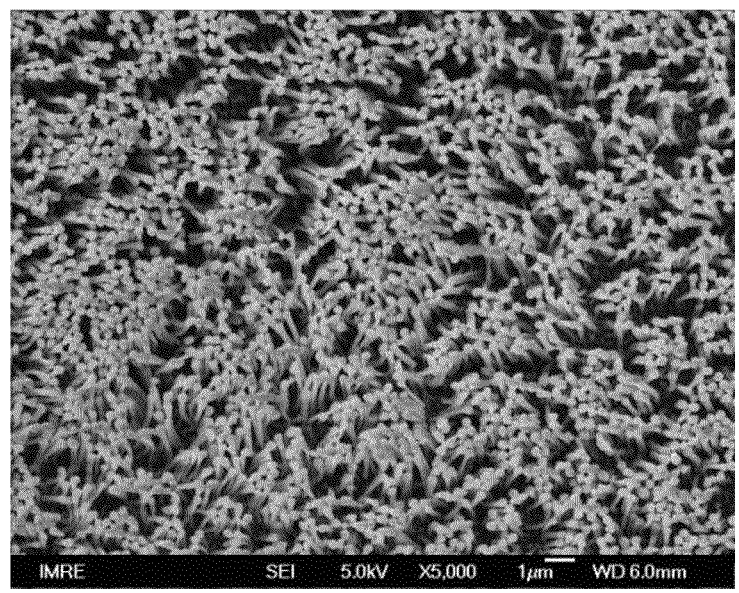
FIG. 10 is a scanning electron microscope image of the DL-PLA substrate comprising 200 nm diameter×2 microns height nanopillars.

The resulting demolded DL-PLA polymer structure comprises pillar-like projections of about 200 nm diameter and about 2 microns length having an aspect ratio (length/diameter) of about 10. FIG. 10 depicts a scanning electron microscope image of the DL-PLA substrate comprising 200 nm diameter×2 microns height pillar-like protrusions.

Example 11

Figure 11:
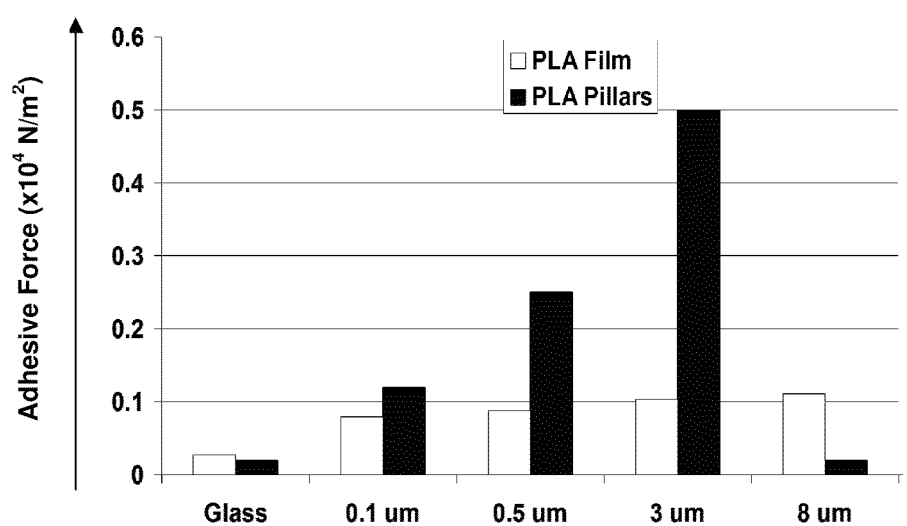
FIG. 11 depicts shear adhesion forces for pillar-like protrusions (0.2 micron diameter and 2 microns length) for PLA as well as its corresponding flat surface film (unpillared) against substrates with varying surface roughness values—flat glass, 0.1 micron, 0.5 micron, 3 microns, and 8 microns.
Figure 12:
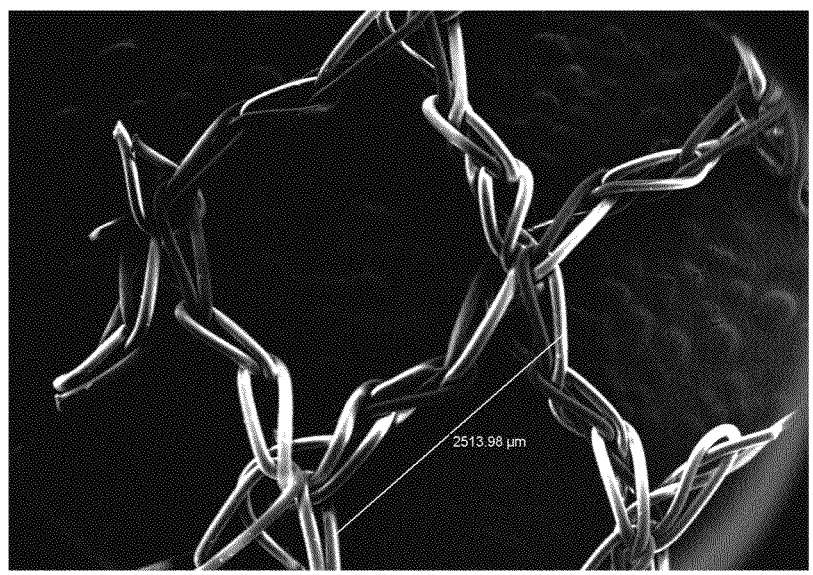
FIG. 12 depicts a SEM image of a bare polypropylene mesh.

The pillared D,L-PLA substrate prepared by the methods of Example 10 as well as its corresponding flat surface film (unpillared) were tested for shear adhesion using the methods of Example 2 against substrates (sandpaper) with varying surface roughness values. The surface roughness value represents the average feature dimensions expected for different surfaces. These tests were performed using a mechanical testing instrument sold under the trade name INSTRON by Instron Industrial Products, Grove City, Pa. The results are summarized in FIG. 11 and clearly showed that the flat, unpatterned PLA films show uniformly low adhesion over all substrate roughnesses. The adhesion of the PLA nanopillars (0.2 micron diameter and 2 microns length) was up to 5 times higher than its flat counterpart, as well as being a function of the substrate roughness. Maximum adhesive force was seen on a substrate roughness of 3 microns which is the nearest to the 2 microns height of the pillar-like protrusions in the structure of Example 10.

Example 12

A polypropylene mesh laminated with a poly(glycolide-co-epsilon-caprolactone) (poliglecaprone 25) film having pillar-like structures was prepared and its effectiveness for attachment to tissue was tested.

First, a poliglecaprone 25 film having pillar-like structures was prepared. A 25 microns thick poliglecaprone 25 film was compressed under heat and pressure with a 20 microns thick sheet of polycarbonate filter material, the thickness of the polycarbonate filter material corresponding to the desired length (or height) of the pillar-like structures to be formed. The filter material possessed microscopic (0.8 micron) holes, which correspond to the eventual diameter of the pillar-like structures to be formed. The membrane filters (0.8 micron ATTP, Cat No. ATTP14250, Lot No. R9SN70958, available from Millipore Corporation of Billerica, Mass., USA) possessed two distinct sides, one having a shiny appearance while the other side was duller. A laminate for compression molding was constructed as follows:

a. A segment of polyimide film (sold under the trade name KAPTON by DuPont, Wilmington, Del.) of 65-70 microns thickness was placed on a table;
b. A 15.2 cm (6 inch) polished square metal plate (thickness 0.8 mm) (shiny side up) was placed on the polyimide film;
c. A segment of polyimide film was placed on the 15.2 cm (6 inch) plate;
d. A 15.2 cm×15.2 cm (6"×6")×80 microns steel shim with a 10.1 cm×10.1 cm (4"×4") cavity in the center was placed on the film;
e. A membrane filter was cut to fit in the shim cavity and was placed (dull side up) on the polyimide film;
f. A piece of 25 microns thick poliglecaprone 25 film was cut to fit in the shim cavity. The sample was placed on the membrane;
g. A segment of polyimide film was placed on the top membrane;
h. A 15.2 cm (6 inch) polished square metal plate (thickness 0.8 mm) (shiny side down) was placed on the polyimide film; and
i. Another segment of polyimide film was placed on the steel plate.

Any thermoformable material as previously described above can be substituted for poliglecaprone 25 as the substrate or core material. The porous solvent-dissolvable polycarbonate filter material which acts as a template for the pillar-like structures of the product can be substituted by another solvent-dissolvable porous polymeric material. Alternately, a strippable mold such as anodized aluminum oxide can be substituted to provide the pillar-like structures of the final product, without the need for exposure to a chemical solvent. Polyimide film was used as a capping means or shield to protect polymer surfaces from directly contacting surfaces such as metal. Other suitable substantially chemically inert materials which can also be provided as a film for this purpose include polytetrafluoroethylene (sold under the trade name TEFLON by DuPont, Wilmington, Del.). Advantageously, these materials are not reactive with the polycarbonate solvent-dissolvable filter material and can be readily removed or peeled therefrom once compression molding is completed.

The above compression molding construct was loaded into a heated compression molding press with vacuum (less than 150 microns mercury) capability and was processed as follows:

a. The top and bottom platens were preheated to 205.5° C. (402° F.);
b. The sample was preheated under vacuum for 300 seconds prior to any compression;
c. The sample was compressed at 68948 kPa (10,000 psi) for 300 seconds;

d. The temperature was reduced to 21° C. (70° F.) while maintaining compression of 68948 kPa (10,000 psi);
e. The compressive force was released and the vacuum was purged; and
f. The sample was removed from the vacuum press.

Using the processing conditions described above, the poliglecaprone 25 film melted and flowed into the holes of the filter material. After processing, the laminate sheet was annealed. The poliglecaprone 25/polycarbonate laminate was annealed in the constrained condition (between two steel plates) in an inert environment (nitrogen gas) at 110° C. for 12.5 hours and then the temperature was slowly reduced to 25° C. over a period of 2.5 hours. Two poliglecaprone 25/polycarbonate laminates were prepared in this manner.

The two poliglecaprone 25/polycarbonate laminates were then laminated to a polypropylene mesh. First, a polypropylene (PP) mesh was prepared as follows. A polypropylene mesh composed of polypropylene and poliglecaprone 25 filaments, sold under the trade name ULTRAPRO (Ethicon, Inc., Somerville, N.J.) was immersed in phosphate buffered saline (PBS) at 37° C. for one week to remove the poliglecaprone 25 filaments from the mesh. Next, a compression molding construct was assembled according to the following:
a. A segment of polyimide film (sold under the trade name KAPTON by DuPont, Wilmington, Del.) of 65-70 microns thickness was placed on a table;
b. A 6 inch square of silicone elastomer (~50 shore A durometer hardness) was placed on the polyimide film;
c. A first poliglecaprone 25/polycarbonate laminate was placed on the square of silicone elastomer (polycarbonate side against the square of silicone);
d. A 7 inch square of PP mesh was placed on top of the poliglecaprone 25/polycarbonate laminate (against the poliglecaprone 25);
e. A 6 inch square of PDO film (37 microns thick) was placed on top of the PP mesh;
f. A second poliglecaprone 25/polycarbonate laminate was placed on top of the PDO film (poliglecaprone 25 against the PDO film);
g. A 6 inch square of silicone elastomer (~50 shore A durometer hardness) was placed on top of the poliglecaprone 25/polycarbonate laminate (against the polycarbonate);
h. A segment of polyimide film was placed on the top of the silicone elastomer.

The above compression molding construct was loaded into a compression molding press with vacuum (less than 150 microns mercury) and was compression molded according to the steps in Table 1.

TABLE 1

PP Mesh Lamination Cycle

| Description | Segment | Time (sec) | Force (lbs) | Vacuum | Platen 1 Temp (F.) | Platen 2 Temp (F.) |
|---|---|---|---|---|---|---|
| Dwell | Preheat | 0 | N/A | On | N/A | N/A |
| Compress | 1 | 600 | 10,000 | On | 233 | 233 |
| Cool | 2 | 1800 | 10,000 | On | 70 | 70 |
| Release F | 3 | 300 | 0 | On | 70 | 70 |
| Release vac | 4 | 300 | 0 | Off | 70 | 70 |
| End of cycle | 5-12 | 0 | 0 | Off | 70 | 70 |

Figure 13:
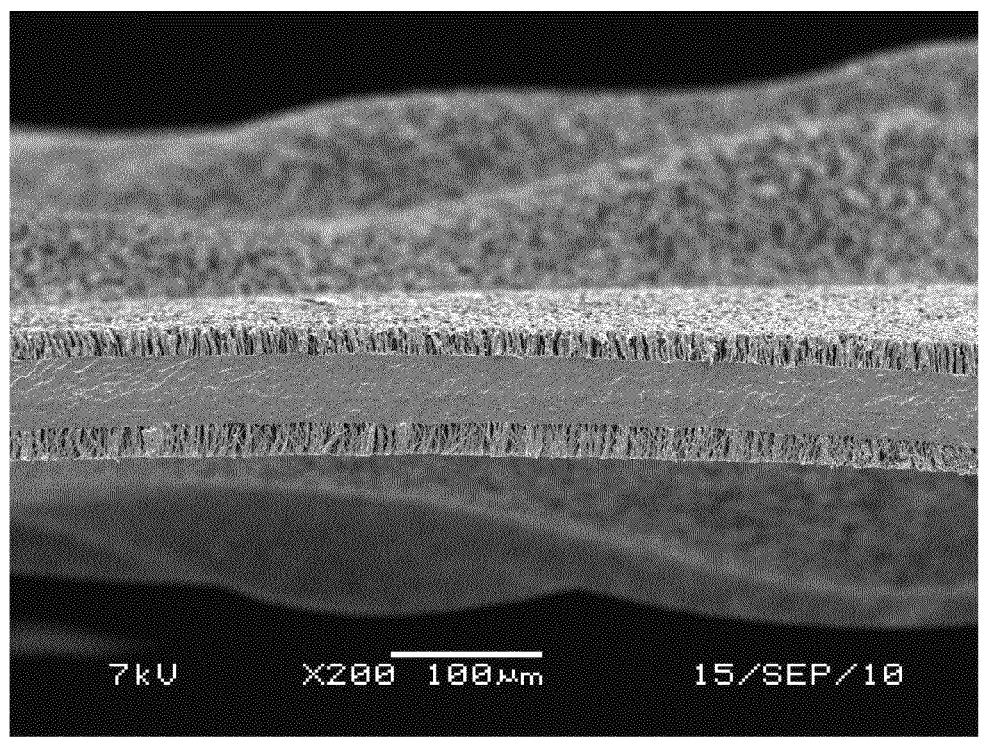
FIG. 13 depicts a SEM image of a mesh laminated with film after the polycarbonate membrane has been dissolved and nanopillars released at low magnification.
Figure 14:
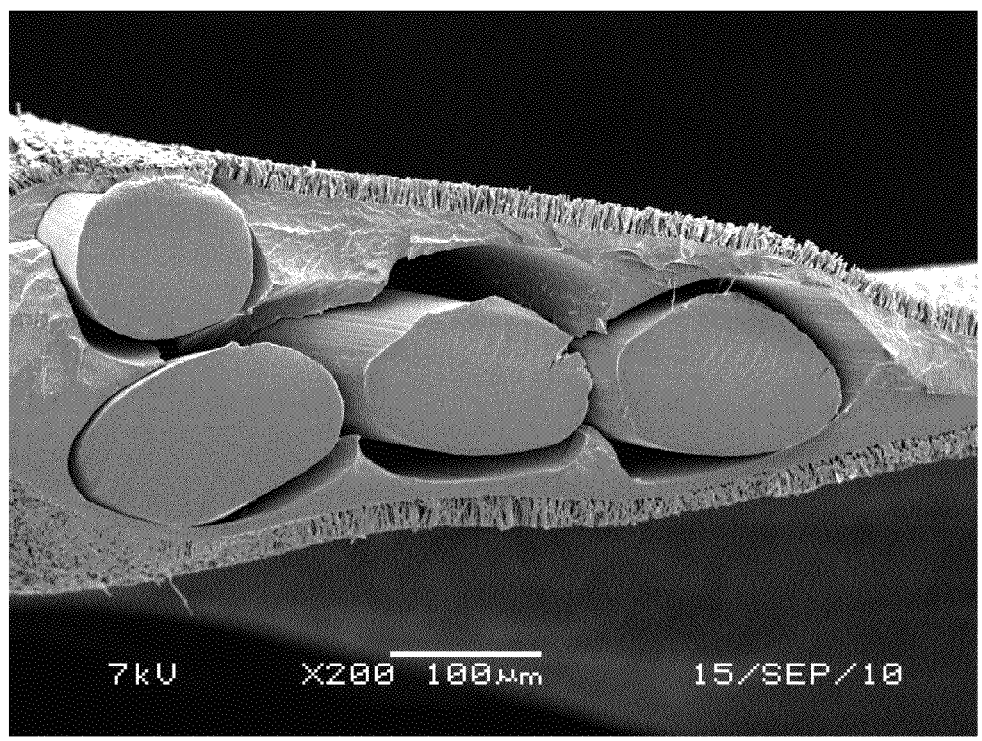
FIG. 14 depicts a SEM image of a mesh laminated with film after the polycarbonate membrane has been dissolved and nanopillars released at high magnification.

The compression molding construct was removed from the press and the poliglecaprone 25/polycarbonate/mesh laminate was separated from the silicone and polyimide films. The polycarbonate membranes were then removed by chemical etching. The poliglecaprone 25/polycarbonate/mesh laminate was immersed in a bath of dichloromethane at room temperature for fifteen minutes. The resulting final poliglecaprone 25 mesh laminate having pillar-like structures was allowed to air dry prior to handling. Scanning electron microscope (SEM) images (FIGS. 13 and 14) confirmed the presence of pillar-like structures made of poliglecaprone 25 which were about 20 microns high and 0.8 microns in diameter.

Figure 15:
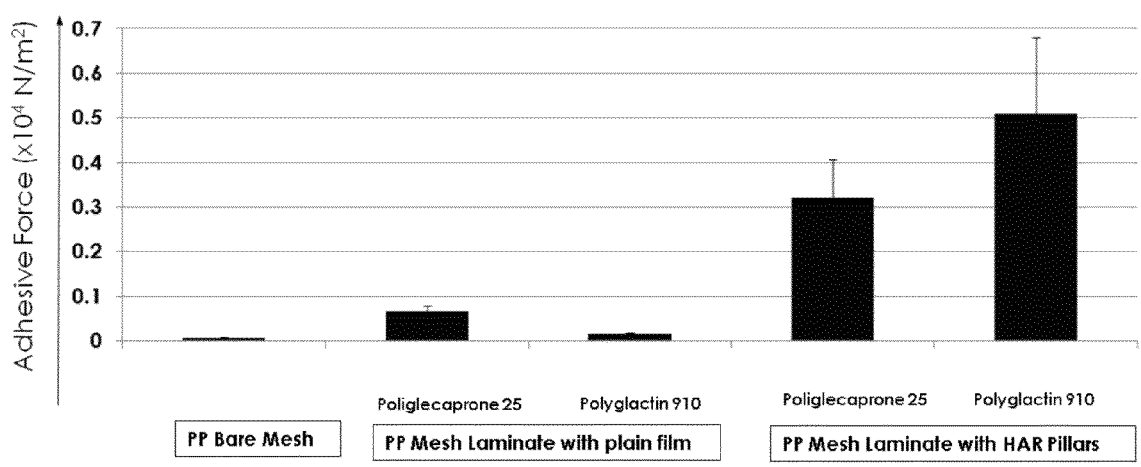
FIG. 15 is a graph which shows the shear adhesion of mesh and mesh laminates to tissue.

Shear adhesion tests were performed on the PP mesh, PP mesh laminated with flat poliglecaprone 25 film, and poliglecaprone 25 mesh laminate having pillar-like structures. The shear adhesion results are shown in FIG. 15 and show enhanced attachment of the poliglecaprone 25 mesh laminate having pillar-like structures.

Example 13

A polypropylene mesh laminated with a polyglactin 910 film having pillar-like structures was prepared and its effectiveness for attachment to tissue was tested.

First, a polyglactin 910 film having pillar-like structures was prepared. A 25 microns thick polyglactin 910 film was compressed under heat and pressure with a 20 microns thick sheet of polycarbonate filter material, the thickness of the polycarbonate filter material corresponds to the desired length (or height) of the pillar-like structures to be formed. The filter material possessed microscopic (0.8 micron) holes, which correspond to the eventual diameter of the pillar-like structures to be formed. The membrane filters (0.8 micron ATTP, Cat No. ATTP14250, Lot No. R9SN70958, available from Millipore Corporation of Billerica, Mass., USA) possessed two distinct sides, one having a shiny appearance while the other side was duller. A laminate for compression molding was constructed as follows:
a. A segment of polyimide film (sold under the trade name KAPTON by DuPont, Wilmington, Del.) of 65-70 microns thickness was placed on a table;
b. A 15.2 cm (6 inch) polished square metal plate (thickness 0.8 mm) (shiny side up) was placed on the polyimide film;
c. A segment of polyimide film was placed on the 15.2 cm (6 inch) plate;
d. A 15.2 cm×15.2 cm (6"×6")×80 microns steel shim with a 10.1 cm×10.1 cm (4"×4") cavity in the center was placed on the film;
e. A membrane filter was cut to fit in the shim cavity and was placed (dull side up) on the polyimide film;
f. A piece of 25 microns thick polyglactin 910 film was cut to fit in the shim cavity. The sample was placed on the membrane;
g. A segment of polyimide film was placed on the top membrane;
h. A 15.2 cm (6 inch) polished square metal plate (thickness 0.8 mm) (shiny side down) was placed on the polyimide film; and
i. Another segment of polyimide film was placed on the steel plate.

Any thermoformable material as previously described above can be substituted for polyglactin 910 as the substrate or core material. The porous solvent-dissolvable polycarbonate filter material which acts as a template for the pillar-like structures of the product can be substituted by another solvent-dissolvable porous polymeric material. Alternately, a strippable mold such as anodized aluminum oxide can be substituted to provide the pillar-like structures of the final product, without the need for exposure to a chemical solvent. Polyimide film was used as a capping means or shield to protect polymer surfaces from directly contacting surfaces such as metal. Other suitable substantially chemically inert materials which can also be provided as a film for this purpose include polytetrafluoroethylene (sold under the trade name TEFLON by DuPont, Wilmington, Del.). Advantageously, these materials are not reactive with the polycarbonate solvent-dissolvable filter material and can be readily removed or peeled therefrom once compression molding is completed.

The above compression molding construct was loaded into a heated compression molding press with vacuum (less than 150 microns mercury) capability and was processed as follows:
   a. The top and bottom platens were preheated to 220° C. (428° F.);
   b. The sample was preheated under vacuum for 300 seconds prior to any compression;
   c. The sample was compressed at 68948 kPa (10,000 psi) for 300 seconds;
   d. The temperature was reduced to 21° C. (70° F.) while maintaining compression of 68948 kPa (10,000 psi);
   e. The compressive force was released and the vacuum was purged; and
   f. The sample was removed from the vacuum press.

Using the processing conditions described above, the polyglactin 910 film melted and flowed into the holes of the filter material. After processing, the laminate sheet was annealed. The polyglactin 910/polycarbonate laminate was annealed in the constrained condition (between two steel plates) in an inert environment (nitrogen gas) at 110° C. for 12.5 hours and then the temperature was slowly reduced to 25° C. over a period of 2.5 hours. Two polyglactin 910/polycarbonate laminates were prepared in this manner.

The two polyglactin 910/polycarbonate laminates were then laminated to a polypropylene mesh. First, a polypropylene (PP) mesh was prepared as follows. A polypropylene mesh composed of polypropylene and polyglactin 910 filaments, sold under the trade name ULTRAPRO (Ethicon, Inc., Somerville, N.J.) was immersed in phosphate buffered saline (PBS) at 37° C. for one week to remove the poliglecaprone 25 filaments from the mesh. Next, a compression molding construct was assembled according to the following:
   a. A segment of polyimide film (sold under the trade name KAPTON by DuPont, Wilmington, Del.) of 65-70 microns thickness was placed on a table;
   b. A 6 inch square of silicone elastomer (~50 shore A durometer hardness) was placed on the polyimide film;
   c. A first polyglactin 910/polycarbonate laminate was placed on the square of silicone elastomer (polycarbonate side against the square of silicone);
   d. A 7 inch square of PP mesh was placed on top of the polyglactin 910/polycarbonate laminate (against the polyglactin 910);
   e. A 6 inch square of PDO film (37 microns thick) was placed on top of the PP mesh;
   f. A second polyglactin 910/polycarbonate laminate was placed on top of the PDO film (polyglactin 910 against the PDO film);
   g. A 6 inch square of silicone elastomer (~50 shore A durometer hardness) was placed on top of the polyglactin 910/polycarbonate laminate (against the polycarbonate);
   h. A segment of polyimide film was placed on the top of the silicone elastomer.

The above compression molding construct was loaded into a compression molding press with vacuum (less than 150 microns mercury) and was compression molded according to the steps in Table 2.

TABLE 2

PP Mesh Lamination Cycle

| Description | Segment | Time (sec) | Force (lbs) | Vacuum | Platen 1 Temp (F.) | Platen 2 Temp (F.) |
|---|---|---|---|---|---|---|
| Dwell | Preheat | 0 | N/A | On | N/A | N/A |
| Compress | 1 | 600 | 10,000 | On | 233 | 233 |
| Cool | 2 | 1800 | 10,000 | On | 70 | 70 |
| Release F | 3 | 300 | 0 | On | 70 | 70 |
| Release vac | 4 | 300 | 0 | Off | 70 | 70 |
| End of cycle | 5-12 | 0 | 0 | Off | 70 | 70 |

The compression molding construct was removed from the press and the polyglactin 910/polycarbonate/mesh laminate was separated from the silicone and polyimide films. The polycarbonate membranes were then removed by chemical etching. The polyglactin 910/polycarbonate/mesh laminate was immersed in a bath of dichloromethane at room temperature for fifteen minutes. The resulting final polyglactin 910 mesh laminate having pillar-like structures was allowed to air dry prior to handling. Scanning electron microscope (SEM) images confirmed the presence of pillar-like structures which were about 20 microns high and 0.8 microns in diameter.

Shear adhesion tests were performed on the PP mesh, PP mesh laminated with polyglactin 910 film, and polyglactin 910 mesh laminate having pillar-like structures. The shear adhesion results are shown in FIG. 15 and show enhanced attachment of the polyglactin 910 mesh laminate having pillar-like structures.

Example 14

A polypropylene mesh laminate with polydioxanone film, having high aspect ratio (HAR) pillars on the surface can be prepared using single step process. A commercial track etched polycarbonate membrane can be obtained from Millipore Corporation of Billerica, Mass., USA having pores of 0.8 microns diameter and a circular diameter of 15 cm, with a thickness of 20 microns. A polypropylene mesh can be placed on top of a polydioxanone film of 25 microns thickness, which can then be pressed into the polycarbonate membrane under controlled temperature and pressure (120° C., 10 bars) for 5 minutes, melting the polydioxanone and filling up the pores. The polydioxanone polymer may be cooled to room temperature before removal of pressure and annealed in a vacuum oven at 70° C. for 3-12 hours, after which the polycarbonate membrane may be dissolved in dichloromethane, releasing the HAR pillars. The final film obtained would be a polypropylene mesh laminated with polydioxanone film having HAR pillars protrusion of 0.8 microns diameter×20 microns length on a single side. Using the same methods, a polypropylene mesh can be laminated on both sides with polydioxanone HAR pillars by pressing a polycarbonate membrane, a thin polydioxanone film, a polypropylene mesh, another thin polydioxanone film and another polycarbonate membrane together under controlled temperature and pressure. After annealing and dissolving the polycarbonate membranes in dichloromethane, a polypropylene mesh laminated with polydioxanone HAR pillars on both sides can be obtained.

All patents, test procedures, and other documents cited herein, including priority documents, are fully incorporated by reference to the extent such disclosure is not inconsistent and for all jurisdictions in which such incorporation is permitted.

When numerical lower limits and numerical upper limits are listed herein, ranges from any lower limit to any upper limit are contemplated.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

What is claimed:

1. A method of forming a laminate of a surgical mesh having first and second surfaces, and an adhesive structure having adhesive and non-adhesive surfaces, comprising:
  a) providing a first solvent-dissolvable mold including indentations;
  b) providing a first meltable polymer having a Young's modulus of greater than 17 MPa to the first mold under conditions sufficient to permit filling the indentations of the first mold by the first polymer, said first polymer being non-dissolvable by the solvent;
  c) treating the first mold and first polymer of step b) to an extent sufficient to solidify the first polymer;
  d) laminating a surgical mesh, also non-dissolvable by said solvent, to an exposed surface of said first meltable polymer at the top of said first mold; and
  e) exposing the first mold, first polymer and surgical mesh to the solvent under mold-dissolving conditions to dissolve said first mold.

2. The method of claim 1, further comprising
  f) providing a second solvent-dissolvable mold including indentations;
  g) providing a second meltable polymer having a Young's modulus of greater than 17 MPa to the second mold under conditions sufficient to permit filling the indentations of the second mold by the second polymer, said second polymer being non-dissolvable by the solvent;
  h) treating the second mold and second polymer of step g) to an extent sufficient to solidify the second polymer;
  i) laminating an exposed surface of said second meltable polymer at the top of said second mold to the surgical mesh; and
  j) exposing both said first and second molds, first and second polymers and the surgical mesh to the solvent under mold-dissolving conditions.

* * * * *